(12) United States Patent
Morriello et al.

(10) Patent No.: US 8,933,102 B2
(45) Date of Patent: Jan. 13, 2015

(54) PYRROLIDINE DERIVED β3 ADRENERGIC RECEPTOR AGONISTS

(75) Inventors: Gregori J. Morriello, Randolph, NJ (US); Lehua Chang, Ramsey, NJ (US); Scott D. Edmondson, Clark, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 76 days.

(21) Appl. No.: 13/881,548

(22) PCT Filed: Oct. 24, 2011

(86) PCT No.: PCT/US2011/057417
§ 371 (c)(1),
(2), (4) Date: Apr. 25, 2013

(87) PCT Pub. No.: WO2012/058130
PCT Pub. Date: May 3, 2012

(65) Prior Publication Data
US 2013/0225599 A1    Aug. 29, 2013

Related U.S. Application Data

(60) Provisional application No. 61/407,759, filed on Oct. 28, 2010.

(51) Int. Cl.
| | | |
|---|---|---|
| A01N 43/40 | (2006.01) |
| A61K 31/445 | (2006.01) |
| A61K 31/497 | (2006.01) |
| A61K 31/4965 | (2006.01) |
| A01N 43/64 | (2006.01) |
| A61K 31/41 | (2006.01) |
| C07D 241/02 | (2006.01) |
| C07D 405/00 | (2006.01) |
| C07D 409/00 | (2006.01) |
| C07D 411/00 | (2006.01) |
| C07D 413/00 | (2006.01) |
| C07D 417/00 | (2006.01) |
| C07D 419/00 | (2006.01) |
| C07D 421/00 | (2006.01) |
| C07D 211/06 | (2006.01) |
| C07D 257/00 | (2006.01) |
| C07D 207/00 | (2006.01) |
| C07D 295/00 | (2006.01) |
| A61K 31/506 | (2006.01) |
| A61K 31/40 | (2006.01) |
| A61K 45/06 | (2006.01) |
| C07D 401/14 | (2006.01) |
| C07D 403/14 | (2006.01) |
| A61K 31/454 | (2006.01) |

(52) U.S. Cl.
CPC ............... *A61K 31/506* (2013.01); *A61K 31/40* (2013.01); *A61K 31/445* (2013.01); *A61K 45/06* (2013.01); *C07D 401/14* (2013.01); *C07D 403/14* (2013.01); *A61K 31/41* (2013.01); *A61K 31/454* (2013.01)
USPC ............ 514/326; 514/252.19; 514/255.01; 514/254.1; 514/330; 514/381; 544/357; 544/406; 546/226; 546/210; 546/211; 548/253; 548/400

(58) Field of Classification Search
USPC .............. 514/252.19, 326, 381, 255.01, 330, 514/254.01; 544/357, 406; 546/226, 210, 546/211; 548/253, 400
See application file for complete search history.

(56) References Cited

U.S. PATENT DOCUMENTS

| 5,451,677 A | 9/1995 | Fischer et al. |
| 5,786,356 A | 7/1998 | Bell et al. |

FOREIGN PATENT DOCUMENTS

WO    WO2009123870 A1    10/2009

*Primary Examiner* — Kendra D Carter
(74) *Attorney, Agent, or Firm* — Patricia A. Shatynski; Laura Ginkel

(57) ABSTRACT

The present invention provides compounds of Formula (I), pharmaceutical compositions thereof, and method of using the same in the treatment or prevention of diseases mediated by the activation of b3-adrenoceptor. Formula (I).

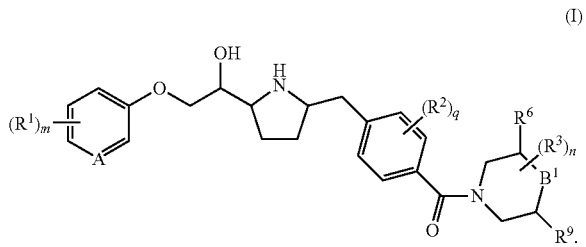

8 Claims, No Drawings

PYRROLIDINE DERIVED β3 ADRENERGIC RECEPTOR AGONISTS

CROSS REFERENCE TO RELATED APPLICATIONS

This application is a U.S. National Phase application under 35 U.S.C. §371 of PCT Application No. PCT/US2011/057417, filed Oct. 24, 2011 which claims priority under 35 U.S.C. §119(e) from U.S. Provisional Application Ser. No. 61/407,759, filed Oct. 28, 2010.

BACKGROUND OF THE INVENTION

The function of the lower urinary tract is to store and periodically release urine. This requires the orchestration of storage and micturition reflexes which involve a variety of afferent and efferent neural pathways, leading to modulation of central and peripheral neuroeffector mechanisms, and resultant coordinated regulation of sympathetic and parasympathetic components of the autonomic nervous system as well as somatic motor pathways. These proximally regulate the contractile state of bladder (detrusor) and urethral smooth muscle, and urethral sphincter striated muscle.

β Adrenergic receptors (βAR) are present in detrusor smooth muscle of various species, including human, rat, guinea pig, rabbit, ferret, dog, cat, pig and non-human primate. However, pharmacological studies indicate there are marked species differences in the receptor subtypes mediating relaxation of the isolated detrusor; β1AR predominate in cats and guinea pig, β2AR predominate in rabbit, and β3AR contribute or predominate in dog, rat, ferret, pig, cynomolgus and human detrusor. Expression of βAR subtypes in the human and rat detrusor has been examined by a variety of techniques, and the presence of β3AR was confirmed using in situ hybridization and/or reverse transcription-polymerase chain reaction (RT-PCR). Real time quantitative PCR analyses of β1AR, β2AR and β3AR mRNAs in bladder tissue from patients undergoing radical cystectomy revealed a preponderance of β3AR mRNA (97%, cf 1.5% for β1AR mRNA and 1.4% for β2AR mRNA). Moreover, β3AR mRNA expression was equivalent in control and obstructed human bladders. These data suggest that bladder outlet obstruction does not result in downregulation of β3AR, or in alteration of β3AR-mediated detrusor relaxation. β3AR responsiveness also has been compared in bladder strips obtained during cystectomy or enterocystoplasty from patients judged to have normal bladder function, and from patients with detrusor hyporeflexia or hyperreflexia. No differences in the extent or potency of β3AR agonist mediated relaxation were observed, consistent with the concept that the β3AR activation is an effective way of relaxing the detrusor in normal and pathogenic states.

Functional evidence in support of an important role for the β3AR in urine storage emanates from studies in vivo. Following intravenous administration to rats, the rodent selective β3AR agonist CL316243 reduces bladder pressure and in cystomeric studies increases bladder capacity leading to prolongation of micturition interval without increasing residual urine volume.

Overactive bladder is characterized by the symptoms of urinary urgency, with or without urgency urinary incontinence, usually associated with frequency and nocturia. The prevalence of OAB in the United States and Europe has been estimated at 16 to 17% in both women and men over the age of 18 years. Overactive bladder is most often classified as idiopathic, but can also be secondary to neurological condition, bladder outlet obstruction, and other causes. From a pathophysiologic perspective, the overactive bladder symptom complex, especially when associated with urge incontinence, is suggestive of detrusor overactivity. Urgency with or without incontinence has been shown to negatively impact both social and medical well-being, and represents a significant burden in terms of annual direct and indirect healthcare expenditures. Importantly, current medical therapy for urgency (with or without incontinence) is suboptimal, as many patients either do not demonstrate an adequate response to current treatments, and/or are unable to tolerate current treatments (for example, dry mouth associated with anticholinergic therapy). Therefore, there is need for new, well-tolerated therapies that effectively treat urinary frequency, urgency and incontinence, either as monotherapy or in combination with available therapies. Agents that relax bladder smooth muscle, such as β3AR agonists, are expected to be effective for treating such urinary disorders.

SUMMARY OF THE INVENTION

The present invention relates to novel β3AR agonists of Formula I,

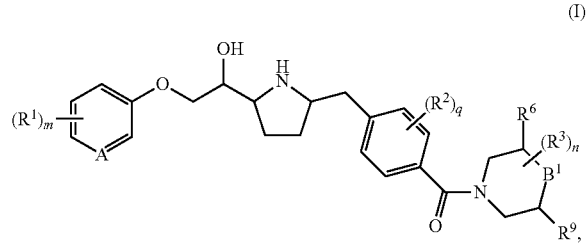

(I)

or pharmaceutical compositions containing them, as well as methods for the treatment or prophylaxis of disorders mediated through the β3AR using such novel compounds.

DESCRIPTION OF THE INVENTION

Described herein are compounds of Formula I, or a pharmaceutically acceptable salt thereof:

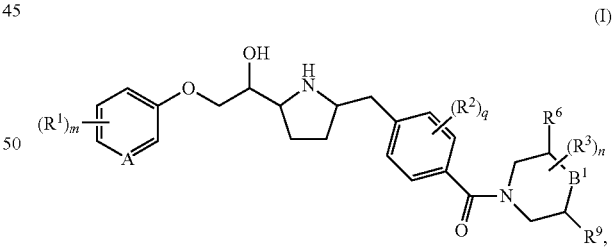

(I)

wherein m is 0 or 1;
n is 0, 1, or 2;
q is 0 or 1;
A is —CH= or —N=;
$B^1$ is —CH$_2$— or NH—;
$R^6$ and $R^9$ are each a hydrogen;
or $R^6$ and $R^9$ form a direct bond;
Z is selected from the group consisting of:
  (1) $C_5$-$C_{10}$ carbocyclic ring, and
  (2) 5- to 6-membered heterocyclic ring with from 1 to 4 heteroatoms selected from oxygen, sulfur and nitrogen, at least one of which is nitrogen;

each occurrence of $R^1$ and $R^2$ is independently selected from the group consisting of:
(1) $C_1$-$C_4$ alkyl optionally substituted with 1 to 3 halogen atoms, and
(2) halogen;
each occurrence of $R^3$ is independently selected from the group consisting of:
(1) $C_1$-$C_4$ alkyl optionally substituted with 1 to 3 groups independently selected from:
(a) halogen,
(b) —$OR^a$, and
(c) Z optionally substituted with 1 to 3 groups independently selected from halogen, $C_1$-$C_4$ alkyl optionally substituted with 1 to 3 halogen atoms,
(2) halogen,
(3) —$OR^a$,
(4) —$NR^aR^b$, and
(5) Z optionally substituted with 1 to 3 groups independently selected from
(a) $C_1$-$C_4$ alkyl optionally substituted with 1 to 3 halogen atoms,
(b) halogen,
(c) —$OR^a$, and
(d) —$NR^aR^b$; and
each occurrence of $R^a$ and $R^b$ is independently selected from the group consisting of:
(1) hydrogen, and
(2) $C_1$-$C_4$ alkyl optionally substituted with 1 to 3 halogen atoms.

In one embodiment, disclosed herein are compounds of Formula I, or a pharmaceutically acceptable salt thereof, wherein:
wherein m is 0 or 1;
n is 0, 1, or 2;
q is 0 or 1;
A is —CH= or —N=;
$B^1$ is —$CH_2$— or —NH—;
$R^6$ and $R^9$ are each a hydrogen;
or $R^6$ and $R^9$ form a direct bond;
Z is a 5- to 6-membered heterocyclic ring with from 1 to 4 nitrogen atoms;
each occurrence of $R^1$ and $R^2$ is independently selected from the group consisting of:
(1) $C_1$-$C_4$ alkyl optionally substituted with 1 to 3 halogen atoms, and
(2) halogen;
each occurrence of $R^3$ is independently selected from the group consisting of:
(1) $C_1$-$C_4$ alkyl optionally substituted with 1 to 3 groups independently selected from:
(a) halogen,
(b) —$OR^a$, and
(c) Z optionally substituted with 1 to 3 groups independently selected from halogen, $C_1$-$C_4$ alkyl optionally substituted with 1 to 3 halogen atoms,
(2) halogen,
(3) —$OR^a$,
(4) —$NR^aR^b$, and
(5) Z optionally substituted with 1 to 3 groups independently selected from
(a) $C_1$-$C_4$ alkyl optionally substituted with 1 to 3 halogen atoms,
(b) halogen,
(c) —$OR^a$, and
(d) —$NR^aR^b$; and
each occurrence of $R^a$ and $R^b$ is independently selected from the group consisting of:
(1) hydrogen, and
(2) $C_1$-$C_4$ alkyl optionally substituted with 1 to 3 halogen atoms.

In another embodiment, disclosed herein is a compound of Formula I, or a pharmaceutically acceptable salt thereof, wherein:
m is 0;
n is 0, 1, or 2;
q is 0;
A is —CH=;
Z is a 5- to 6-membered heterocyclic ring with from 1 to 4 nitrogen atoms;
each occurrence of $R^3$ is independently selected from the group consisting of:
(1) $C_1$-$C_4$ alkyl optionally substituted with 1 to 3 groups independently selected from:
(a) halogen,
(b) —$OR^a$, and
(c) Z optionally substituted with 1 to 3 groups independently selected from halogen, $C_1$-$C_4$ alkyl optionally substituted with 1 to 3 halogen atoms,
(2) halogen, and
(3) Z optionally substituted with 1 to 3 groups independently selected from
(a) $C_1$-$C_4$ alkyl optionally substituted with 1 to 3 halogen atoms,
(b) halogen,
(c) —$OR^a$, and
(d) —$NR^aR^b$; and
each occurrence of $R^a$ and $R^b$ is independently selected from the group consisting of:
(1) hydrogen,
(2) methyl, and
(3) ethyl.

In yet another embodiment, disclosed herein is a compound of Formula I, or a pharmaceutically acceptable salt thereof, wherein:
m is 0;
n is 0 or 1;
q is 0;
A is —CH=;
Z is selected from the group consisting of pyridyl, dihydropyridyl, 1,2,4-triazolyl, 1,2,3-triazolyl, tetrazolyl, pyrimidinyl, dihydropyrimidinyl, tetrahydropyrimidinyl, pyrazinyl, dihydropyrazinyl, pyridazinyl, dihydropyridazinyl, pyrrolidinyl, imidazolyl, pyrazolyl;
each occurrence of $R^3$ is independently selected from the group consisting of:
(1) $C_1$-$C_4$ alkyl optionally substituted with 1 to 2 groups independently selected from:
(a) halogen, and
(b) Z optionally substituted with 1 to 3 groups independently selected from halogen and $C_1$-$C_4$ alkyl,
(2) halogen, and
(3) Z optionally substituted with 1 to 3 groups independently selected from
(a) $C_1$-$C_4$ alkyl, and
(b) halogen.

In still another embodiment, disclosed herein is a compound of Formula I, or a pharmaceutically acceptable salt thereof, wherein:
m is 0;
n is 0 or 1;
q is 0;
A is —CH=;
Z is selected from the group consisting of pyridyl, dihydropyridyl, 1,2,4-triazolyl, 1,2,3-triazolyl, tetrazolyl, pyrimidinyl, dihydropyrimidinyl, tetrahydropyrimidinyl, pyrazinyl, dihydropyrazinyl, pyridazinyl, dihydropyridazinyl, pyrrolidinyl, imidazolyl, pyrazolyl; and $R^3$ is selected from the group consisting of:
  (1) $C_1$-$C_4$ alkyl optionally substituted with 1 to 2 Z groups, and
  (2) Z optionally substituted with 1 to 2 $C_1$-$C_4$ alkyl groups.

In one embodiment, disclosed herein is a compound of Formula Ia, or a pharmaceutically acceptable salt thereof, wherein:

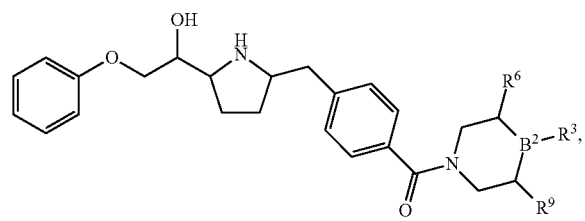

(Ia)

wherein $B^2$ is —CH— or —N—;

$R^6$ and $R^9$ are each a hydrogen;

or $R^6$ and $R^9$ form a direct bond;

Z is selected from the group consisting of pyridyl, dihydropyridyl, 1,2,4-triazolyl, 1,2,3-triazolyl, tetrazolyl, pyrimidinyl, dihydropyrimidinyl, tetrahydropyrimidinyl, pyrazinyl, dihydropyrazinyl, pyridazinyl, dihydropyridazinyl, pyrrolidinyl, imidazolyl, pyrazolyl; and $R^3$ is selected from the group consisting of:
  (1) methyl optionally substituted with 1 to 2 Z groups,
  (2) ethyl optionally substituted with 1 to 2 Z groups; and
  (3) Z optionally substituted with 1 to 2 groups independently selected from methyl, ethyl, propyl and halogen.

In another embodiment, disclosed herein is a compound of Formula Ia, or a pharmaceutically acceptable salt thereof, wherein:

$B^2$ is —CH—;

Z is selected from the group consisting of pyridyl, dihydropyridyl, 1,2,4-triazolyl, 1,2,3-triazolyl, tetrazolyl, pyrimidinyl, dihydropyrimidinyl, tetrahydropyrimidinyl, pyrazinyl, dihydropyrazinyl, and pyridazinyl; and $R^3$ is Z optionally substituted with 1 to 2 groups independently selected from methyl, ethyl, propyl and halogen.

In one embodiment, disclosed herein is a compound of Formula (Ib), or a pharmaceutically acceptable salt thereof, wherein R is selected from the following table:

In one embodiment, disclosed herein is a pharmaceutical composition comprising a compound of Formula I, Ia or Ib and a pharmaceutically acceptable carrier.

In another embodiment, disclosed herein is a method for the treatment or prevention of a disease or disorder mediated by the activation of β3-adrenoceptor, wherein said method comprises administering to a patient in need thereof a therapeutically effective amount of a compound of Formula I, Ia or Ib.

In one embodiment, the disease or disorder mediated by the activation of β3-adrenoceptor is selected from the group consisting of (1) overactive bladder, (2) urinary incontinence, (3) urge urinary incontinence, and (4) urinary urgency.

In one embodiment, disclosed herein is a method for the treatment or prevention of a disease or disorder mediated by the activation of β3-adrenoceptor, wherein the method comprises administering to a patient in need thereof a therapeutically effective amount of a compound of Formula I, Ia or Ib and a second active agent.

In one embodiment, disclosed herein is the use of a compound of Formula I, Ia or Ib in the manufacture of a medicament for the treatment or prevention of a disease or disorder mediated by the activation of β3-adrenoceptor.

As used herein, the term "alkyl" means both branched- and straight-chain saturated aliphatic hydrocarbon groups having the specified number of carbon atoms. For example, $C_1$-$C_6$ alkyl includes, but is not limited to, methyl (Me), ethyl (Et), n-propyl (Pr), n-butyl (Bu), n-pentyl, n-hexyl, and the isomers thereof such as isopropyl (i-Pr), isobutyl (i-Bu), secbutyl (s-Bu), tert-butyl (t-Bu), isopentyl, sec-pentyl, tert-pentyl, isohexyl and the like.

The term "cycloalkyl" means a monocyclic saturated carbocyclic ring, having the specified number of carbon atoms, e.g., 3, 4, 5 or 6 carbon atoms. Non-limiting examples of $C_3$-$C_6$ cycloalkyl include cyclopropyl, cyclobutyl, cyclopentyl and cyclohexyl.

The term "optionally substituted" means "unsubstituted or substituted," and therefore, the generic structural Formulas described herein encompass compounds containing the specified optional substituent as well as compounds that do not contain the optional substituent. Each variable is independently defined each time it occurs within the generic structural formula definitions.

The terms "halo" or "halogen" are meant to include fluoro, chloro, bromo and iodo, unless otherwise noted.

The terms "carbocycle" or "carbocyclic" refer to saturated, partially unsaturated and aromatic rings having only ring carbon atoms. For examples, $C_1$-$C_6$ carbocyclic ring include, but are not limited to, cyclopentyl, cyclohexyl, cycloheptyl, cyclooctyl, cyclopentenyl, cyclohexenyl, cyclohexadienyl, and phenyl.

The term "aryl" refers to an aromatic carbocycle. For examples, an aryl includes, but is not limited to phenyl and naphthale.

The terms "heterocycle" or "heterocyclic" refer to saturated, partially unsaturated and aromatic rings having at least one ring heteroatom and at least one ring carbon atom; the heterocycle may be attached to the rest of the molecule via a ring carbon atom or a ring hetero atom, for example, a ring nitrogen atom. The terms "heteroaryl" or "heteroaromatic" refer to an aromatic heterocycle. For example, within the definition for Z, the term "a 5- or 6-membered heterocyclic ring with from 1 to 4 heteroatoms selected from oxygen, sulfur and nitrogen" includes, but is not limited to, pyrrolyl, thienyl, furanyl, imidazolyl, pyrazolyl, oxazolyl, isoxazolyl, thiazolyl, isothiazolyl, triazolyl, tetrazolyl, oxadiazolyl, thiadiazolyl, pyrrolidinyl, tetrahydrofuranyl, pyridinyl, dihydropyridinyl, tetrahydropyridinyl, pyrimidinyl, dihydropyrimidinyl, tetrahydropyrimidinyl, pyrazinyl, dihydropyrazinyl, tetrahydropyrazinyl, pyridazinyl, dihydropyridazinyl, tetrahydropyridazinyl, piperidinyl, piperazinyl, morpholinyl, pyranyl, dihydropyranyl, tetrahydropyranyl, and the like.

Within the definition for Z, the term "a benzene ring fused to a $C_5$-$C_{10}$ carbocyclic ring" includes, but is not limited to, naphthyl, dihydronaphthyl, tetrahydronaphthyl, indanyl, indenyl, benzocycloheptene, tetrahydrobenzocyloheptene, and the like. In one embodiment, a benzene ring is fused to a $C_5$-$C_6$ carbocyclic ring. Such fused ring may be attached to the rest of the molecule via a carbon atom on either ring.

Within the definition for Z, the term "a 5- or 6-membered heterocyclic ring with from 1 to 4 heteroatoms selected from oxygen, sulfur and nitrogen fused to a 5- or 6-membered heterocyclic ring with from 1 to 4 heteroatoms selected from oxygen, sulfur and nitrogen" includes, but is not limited to, naphthyridinyl, dihydronaphthyridinyl, tetrahydronaphthyridinyl, imidazopyridinyl, pteridinyl, purinyl, quinolizinyl, indolizinyl, tetrahydroquinolizinyl, and tetrahydroindolizinyl. In one embodiment, Z is selected from the group consisting of:

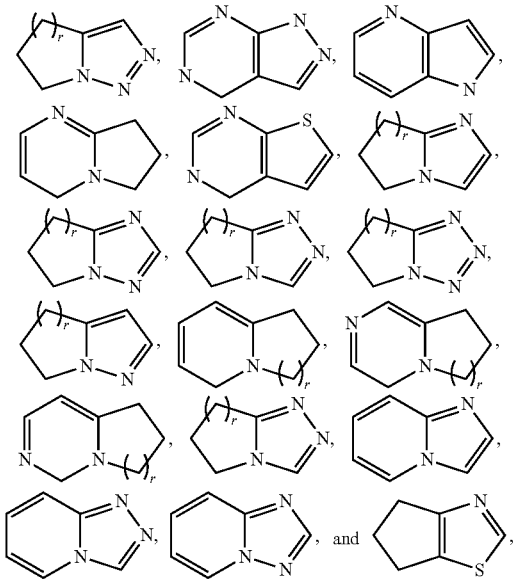

wherein r is 1 or 2. Such fused ring may be attached to the rest of the molecule via a carbon atom or a nitrogen atom on either ring.

To avoid any doubt, the term "a 5- or 6-membered heterocyclic ring with from 1 to 4 heteroatoms selected from oxygen, sulfur and nitrogen fused to a 5- or 6-membered heterocyclic ring with from 1 to 4 heteroatoms selected from oxygen, sulfur and nitrogen" as used herein includes compounds having only one nitrogen as the sole heteroatom when the nitrogen is located at the bridgehead.

Within the definition for Z, the term "a 5- or 6-membered heterocyclic ring with from 1 to 4 heteroatoms selected from oxygen, sulfur and nitrogen fused to a $C_5$-$C_{10}$ carbocyclic ring" includes, but is not limited to, indolyl, isoindolyl, benzofuranyl, benzothienyl, benzimidazolyl, benzotriazolyl, benzoxazolyl, benzisoxazolyl, benzthiazolyl, benzisothiazolyl, quinolinyl, isoquinolinyl, quinoxalinyl, quinazolinyl, cinnolinyl, indazolyl, tetrahydroquinolinyl, tetrahydroindazolyl, dihydroindazolyl, chromenyl, chromanyl benztriazolyl,

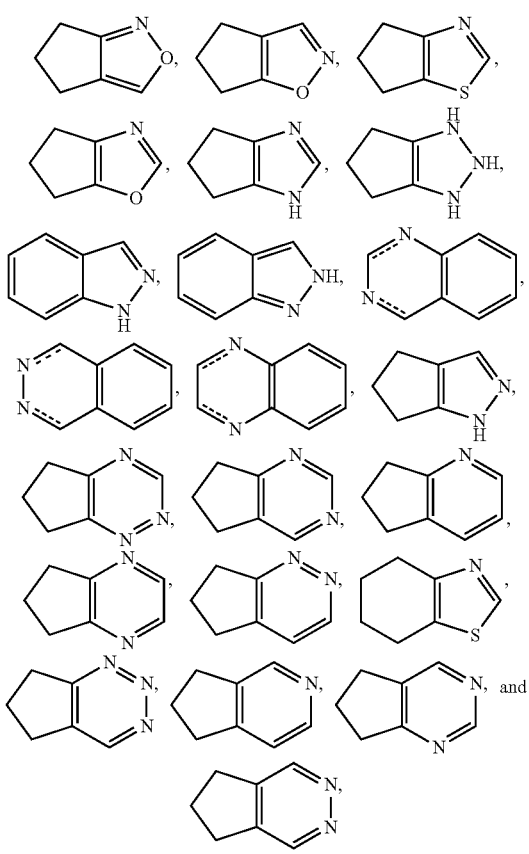

where the dash bond "----" means a single or double bond while conforming to the valency rule for the ring atoms. Such fused ring may be attached to the rest of the molecule via a carbon atom on either ring or a nitrogen atom on the heterocyclic ring.

For the terms $(R^1)_m$, $(R^2)_q$, $(R^3)_n$, as well as other similar notations, when m or q or n is 0, then $R^1$, $R^2$ or $R^3$ is hydrogen; when m, q or n is greater than 1, then each occurrence of $R^1$, $R^2$ or $R^3$ is independently selected from other occurrences of $R^1$, $R^2$ or $R^3$, respectively. For example, when n is 2, the two $R^3$ substituents can be the same or different.

Optical Isomers—Diastereomers—Geometric Isomers—Tautomers

Compounds described herein may contain an asymmetric center and may thus exist as enantiomers. Where the compounds according to the invention possess two or more asymmetric centers, they may additionally exist as diastereomers. When bonds to the chiral carbon are depicted as straight lines in the formulas of the invention, it is understood that both the (R) and (S) configurations of the chiral carbon, and hence both enantiomers and mixtures thereof, are embraced within the formulas. The present invention includes all such possible stereoisomers as substantially pure resolved enantiomers, racemic mixtures thereof, as well as mixtures of diastereomers. The above Formulas I and Ia are shown without a definitive stereochemistry at certain positions. The present invention includes all stereoisomers of Formulas I and Ia and pharmaceutically acceptable salts thereof.

Diastereoisomeric pairs of enantiomers may be separated by, for example, fractional crystallization from a suitable solvent, and the pair of enantiomers thus obtained may be separated into individual stereoisomers by conventional means, for example by the use of an optically active acid or base as a resolving agent or on a chiral HPLC column. Further, any enantiomer or diastereomer of a compound described herein may be obtained by stereospecific synthesis using optically pure starting materials or reagents of known configuration.

When compounds described herein contain olefinic double bonds, unless specified otherwise, such double bonds are meant to include both E and Z geometric isomers.

Some of the compounds described herein may exist with different points of attachment of hydrogen, referred to as tautomers. For example, compounds including carbonyl —$CH_2C(O)$— groups (keto forms) may undergo tautomerism to form hydroxyl —CH=C(OH)— groups (enol forms). Both keto and enol forms, individually as well as mixtures thereof, are included within the scope of the present invention.

Isotopes

In the compounds disclosed herein, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds disclosed herein. For example, different isotopic forms of hydrogen (H) include protium ($^1H$) and deuterium ($^2H$). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds disclosed herein can be prepared without undue experimentation by conventional techniques well known to those skilled in the art or by processes analogous to those described in the Schemes and Examples herein using appropriate isotopically-enriched reagents and/or intermediates.

Salts

The term "pharmaceutically acceptable salts" refers to salts prepared from pharmaceutically acceptable non-toxic bases or acids. When the compound of the present invention is acidic, its corresponding salt can be conveniently prepared from pharmaceutically acceptable non-toxic bases, including inorganic bases and organic bases. Salts derived from such inorganic bases include aluminum, ammonium, calcium, copper (ic and ous), ferric, ferrous, lithium, magnesium, manganese (ic and ous), potassium, sodium, zinc and the like salts. Preferred are the ammonium, calcium, magnesium, potassium and sodium salts. Salts prepared from pharmaceutically acceptable organic non-toxic bases include salts of primary, secondary, and tertiary amines derived from both naturally occurring and synthetic sources. Pharma-ceutically acceptable organic non-toxic bases from which salts can be formed include, for example, arginine, betaine, caffeine, choline, N,N'-dibenzylethylenediamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, dicyclohexylamine, lysine, methylglucamine, morpholine, piperazine, piperidine, polyamine resins, procaine, purines, theobromine, triethylamine, trimethylamine, tripropylamine, tromethamine and the like.

When the compound of the present invention is basic, its corresponding salt can be conveniently prepared from pharmaceutically acceptable non-toxic inorganic and organic acids. Such acids include, for example, acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid and the like. Preferred are citric, hydrobromic, hydrochloric, maleic, phosphoric, sulfuric, and tartaric acids.

Solvates

The present invention includes within its scope solvates of compounds of Formulas I and Ia. As used herein, the term "solvate" refers to a complex of variable stoichiometry formed by a solute (i.e., a compound of Formula I or Ia) or a pharmaceutically acceptable salt thereof and a solvent that does not interfere with the biological activity of the solute. Examples of solvents include, but are not limited to water, ethanol, and acetic acid. When the solvent is water, the solvate is known as hydrate; hydrates include, but are not limited to, hemi-, mono, sesqui-, di- and trihydrates.

Prodrugs

The present invention includes within its scope the use prodrugs of the compounds of this invention. In general, such prodrugs will be functional derivatives of the compounds of this invention which are readily convertible in vivo into the required compound. Thus, in the methods of treatment of the present invention, the term "administering" shall encompass the treatment of the various conditions described with a compound described herein or with a compound which may not be a compound described herein, but which converts to a compound described herein in vivo after administration to the patient. Conventional procedures for the selection and preparation of suitable prodrug derivatives are described, for example, in "Design of Prodrugs," ed. H. Bundgaard, Elsevier, 1985.

Utilities

Compounds of the present invention are potent agonists of the β3-adrenoceptor, and as such are useful in treating or preventing diseases, disorders or conditions mediated by the activation of β3-adrenoceptor. Thus one aspect of the present invention provides a method for the treatment, control or prevention of such diseases, disorders, or conditions in a mammal which comprises administering to such mammal a therapeutically effective amount of a compound described herein. The term "mammal" includes human and non-human animals such as dogs and cats and the like. The diseases, disorders or conditions for which compounds of the present invention are useful in treating or preventing include, but are not limited to, (1) overactive bladder, (2) urinary incontinence, (3) urge urinary incontinence, (4) urinary urgency, (5) diabetes mellitus, (6) hyperglycemia, (7) obesity, (8) hyperlipidemia, (9) hypertriglyceridemia, (10) hypercholesterolemia, (11) atherosclerosis of coronary, cerebrovascular and peripheral arteries, (12) gastrointestinal disorders including peptid ulcer, esophagitis, gastritis and duodenitis, (including that induced by *H. pylori*), intestinal ulcerations (including inflammatory bowel disease, ulcerative colitis, Crohn's disease and proctitis) and gastrointestinal ulcerations, (13) neurogenic inflammation of airways, including cough, asthma, (14) depression, (15) prostate diseases such as benign prostate hyperplasia, (16) irritable bowel syndrome and other disorders needing decreased gut motility, (17) diabetic retinopathy, (18) preterm labor, and (19)-elevated intraocular pressure and glaucoma.

Any suitable route of administration may be employed for providing a mammal, especially a human with an effective dosage of a compound of the present invention. For example, oral, rectal, topical, parenteral, ocular, pulmonary, nasal, and the like may be employed. Dosage forms include tablets, troches, dispersions, suspensions, solutions, capsules, creams, ointments, aerosols, and the like. Preferably compounds described herein are administered orally.

The effective dosage of active ingredient employed may vary depending on the particular compound employed, the mode of administration, the condition being treated and the severity of the condition being treated. Such dosage may be ascertained readily by a person skilled in the art.

When treating overactive bladder (OAB) in conjunction with other anti-OAB agents, or alone, generally satisfactory results are obtained when the compounds of the present invention are administered at a daily dosage of from 0.01 mg to about 100 mg per kg of animal body weight, preferably given in a single dose or in divided doses two to six times a day, or in sustained release form. In the case of a 70 kg adult human, the total daily dose will generally be from about 0.7 mg to about 3500 mg, or more specifically, from about 0.7 mg to about 2000 mg. This dosage regimen may be adjusted to provide the optimal therapeutic response.

When treating obesity, in conjunction with diabetes and/or hyperglycemia, or alone, generally satisfactory results are obtained when the compounds of the present invention are administered at a daily dosage of from 0.01 mg to about 100 mg per kg of animal body weight, preferably given in a single dose or in divided doses two to six times a day, or in sustained release form. In the case of a 70 kg adult human, the total daily dose will generally be from about 0.7 mg to about 3500 mg. This dosage regimen may be adjusted to provide the optimal therapeutic response.

When treating diabetes mellitus and/or hyperglycemia, as well as other diseases or disorders for which compounds described herein are useful, generally satisfactory results are obtained when the compounds of the present invention are administered at a daily dosage of from about 0.001 mg to about 100 mg per kg of animal body weight, preferably given in a single dose or in divided doses two to six times a day, or in sustained release form. In the case of a 70 kg adult human, the total daily dose will generally be from about 0.07 mg to about 350 mg. This dosage regimen may be adjusted to provide the optimal therapeutic response.

In one embodiment, a compound of the present invention is used in the manufacture of a medicament for the treatment or prevention of a disease or disorder mediated by the activation of β3-adrenoceptor.

Another aspect of the present invention provides pharmaceutical compositions which comprises a compound described herein and a pharmaceutically acceptable carrier. The pharmaceutical compositions of the present invention comprise a compound described herein as an active ingredient or a pharmaceutically acceptable salt thereof, and may also contain a pharmaceutically acceptable carrier and optionally other therapeutic ingredients. The term "pharmaceutically acceptable salts" refers to salts prepared from pharmaceutically acceptable non-toxic bases or acids including inorganic bases or acids and organic bases or acids.

The compositions include compositions suitable for oral, intravesical, rectal, topical, parenteral (including subcutaneous, intramuscular, and intravenous), ocular (ophthalmic), pulmonary (nasal or buccal inhalation), or nasal administration, although the most suitable route in any given case will depend on the nature and severity of the conditions being treated and on the nature of the active ingredient. They may be conveniently presented in unit dosage form and prepared by any of the methods well-known in the art of pharmacy.

In practical use, the compounds described herein can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as, for example, water, glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, hard and soft capsules and tablets, with the solid oral preparations being preferred over the liquid preparations.

Because of their ease of administration, tablets and capsules represent the most advantageous oral dosage unit form in which case solid pharmaceutical carriers are obviously employed. If desired, tablets may be coated by standard aqueous or nonaqueous techniques. Such compositions and preparations should contain at least 0.1 percent of active compound. The percentage of active compound in these compositions may, of course, be varied and may conveniently be between about 2 percent to about 60 percent of the weight of the unit. The amount of active compound in such therapeutically useful compositions is such that an effective dosage will be obtained. The active compounds can also be administered intranasally as, for example, liquid drops or spray.

The tablets, pills, capsules, and the like may also contain a binder such as gum tragacanth, acacia, corn starch or gelatin; excipients such as dicalcium phosphate; a disintegrating agent such as corn starch, potato starch, alginic acid; a lubricant such as magnesium stearate; and a sweetening agent such as sucrose, lactose or saccharin. When a dosage unit form is a capsule, it may contain, in addition to materials of the above type, a liquid carrier such as a fatty oil.

Various other materials may be present as coatings or to modify the physical form of the dosage unit. For instance, tablets may be coated with shellac, sugar or both. A syrup or elixir may contain, in addition to the active ingredient, sucrose as a sweetening agent, methyl and propylparabens as preservatives, a dye and a flavoring such as cherry or orange flavor.

Compounds described herein may also be administered parenterally. Solutions or suspensions of these active compounds can be prepared in water suitably mixed with a surfactant such as hydroxy-propylcellulose. Dispersions can also be prepared in glycerol, liquid polyethylene glycols and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g. glycerol, propylene glycol and liquid polyethylene glycol), suitable mixtures thereof, and vegetable oils.

Compounds described herein may be used in combination with other drugs that are used in the treatment/prevention/suppression or amelioration of the diseases or conditions for which compounds described herein are useful. Such other drugs may be administered, by a route and in an amount commonly used therefor, contemporaneously or sequentially with a compound described herein. When a compound described herein is used contemporaneously with one or more other drugs, a pharmaceutical unit dosage form containing such other drugs in addition to the compound described herein is preferred. Accordingly, the pharmaceutical compositions of the present invention include those that also contain one or more other active ingredients, in addition to a compound described herein. Examples of other active ingredients that may be combined with a compound described herein, either administered separately or in the same pharmaceutical compositions, include, but are not limited to:

(a) overactive bladder medicines including (i) muscarinic receptor antagonists (e.g. tolterodine, oxybutynin including 5-oxybutynin, hyoscyamine, propantheline, propiverine, trospium including trospium chloride, solifenacin, darifenacin, imidafenacin, fesoterodine, temiverine, SVT-40776, 202405 by GlaxoSmithKline, TD6301, RBX9841, DDP200, PLD179, and other anticholinergics. See, for example, U.S. Pat. Nos. 5,382,600; 3,176,019; 3,480,626; 4,564,621; 5,096,890; 6,017,927; 6,174,896; 5,036,098; 5,932,607; 6,713,464; 6,858,650; and DD 106643. See also, U.S. Pat. No. 6,103,747; 6,630,162; 6,770,295; 6,911,217; 5,164,190; 5,601,839; 5,834,010; 6,743,441; WO2002000652; WO200400414853. As will be appreciated by those of skill in the art, these drugs may be administered orally or topically in standard or extended release forms, such as extended release tolterodine, extended release oxybutynin and transdermal oxybutynin), (ii) NK-1 or NK-2 antagonists (e.g. aprepitant, cizolirtine, compounds disclosed in WO2005/073191, WO2005/032464, and other reported NK-1 antagonists), (iii) alpha adrenergic receptor antagonists (e.g. alfuzosin, doxazosin, prazosin, tamsulosin, terazosin, and others), (iv) potassium channel openers (e.g. cromakalim, pinacidil, and others), (v) vanilloids and other afferent-nerve modulators—agonists and antagonists (e.g. capsaicin, resiniferatoxin, and others), (vi) dopamine D1 receptor agonists (e.g. pergolinde), (vii) serotonergic and/or norepinephrine reuptake inhibitors (e.g. duloxetine), (viii) neuromuscular junction inhibition of acetylcholine release (e.g. botulinum toxin), (ix) calcium channel blockers (e.g. diltiazem, nifedipine, verapamil, and others), (x) inhibitors of prostaglandin synthesis (e.g. flurbiprofen), (xi) gamma aminobutyric acid receptor antagonists (e.g. baclofen), (xii) vaginal estrogen preparations (xiii) selective norepinephrine reuptake inhibitors, (xiv) 5-HT2C agonists, (xv) voltage gated sodium channel blocker, (xvi) P2X purinergic receptor antagonists (e.g. P2X1 or P2X3 antagonists), (xvii) PAR2 inhibitors, (xviii) phosphodiesterase inhibitors (e.g. PDE1, PDE4, and PDE5 inhibitors); and (xix) ATP sensitive potassium channel openers.

(b) insulin sensitizers including (i) PPARγ agonists such as the glitazones (e.g. troglitazone, pioglitazone, englitazone, MCC-555, BRL49653 and the like), and compounds disclosed in WO97/27857, 97/28115, 97/28137 and 97/27847; (ii) biguanides such as metformin and phenformin;

(c) insulin or insulin mimetics;

(d) sulfonylureas such as tolbutamide and glipizide;

(e) α-glucosidase inhibitors (such as acarbose), (f) cholesterol lowering agents such as (i) HMG-CoA reductase inhibitors (lovastatin, simvastatin and pravastatin, fluvastatin, atorvastatin, and other statins), (ii) sequestrants (cholestyramine, colestipol and a dialkylaminoalkyl derivatives of a cross-linked dextran), (ii) nicotinyl alcohol nicotinic acid or a salt thereof, (iii) proliferator-activater receptor a agonists such as fenofibric acid derivatives (gemfibrozil, clofibrat, fenofibrate and benzafibrate), (iv) inhibitors of cholesterol absorption for example beta-sitosterol and ezetimibe, and (acyl CoA:cholesterol acyltransferase) inhibitors for example melinamide, (v) probucol, (vi) vitamin E, and (vii) thyromimetics;

(g) PPARδ agonists such as those disclosed in WO97/28149;

(h) antiobesity compounds such as fenfluramine, dexfenfluramine, phentermine, sibutramine, orlistat, and other β$_3$ adrenergic receptor agonists;

(i) feeding behavior modifying agents such as neuropeptide Y antagonists (e.g. neuropeptide Y5) such as those disclosed in WO 97/19682, WO 97/20820, WO 97/20821, WO 97/20822 and WO 97/20823;

(j) PPARα agonists such as described in WO 97/36579 by Glaxo;

(k) PPARγ antagonists as described in WO97/10813; and (l) serotonin reuptake inhibitors such as fluoxetine and sertraline.

In one embodiment, a compound of the present invention and a second active agent as described above are used in the manufacture of a medicament for the treatment or prevention of a disease or disorder mediated by the activation of β3-adrenoceptor.

The compounds of disclosed herein can be prepared according to the procedures of the following Schemes and Examples using appropriate materials, and are further exemplified by the following specific examples. Moreover, by utilizing the procedures described herein, one of ordinary skill in the art can readily prepare additional compounds of the present invention claimed herein. The compounds illustrated in the examples are not, however, to be construed as forming the only genus that is considered as the invention. The Examples further illustrate details for the preparation of the compounds of the present invention. Those skilled in the art will readily understand that known variations of the conditions and processes of the following preparative procedures can be used to prepare these compounds. The instant compounds are generally isolated in the form of their pharmaceutically acceptable salts, such as those described previously hereinabove. The free amine bases corresponding to the isolated salts can be generated by neutralization with a suitable base, such as aqueous sodium hydrogen carbonate, sodium carbonate, sodium hydroxide, and potassium hydroxide, and extraction of the liberated amine free base into an organic solvent followed by evaporation. The amine free base isolated in this manner can be further converted into another pharmaceutically acceptable salt by dissolution in an organic solvent followed by addition of the appropriate acid and subsequent evaporation, precipitation, or crystallization. All temperatures are degrees Celsius unless otherwise noted. Mass spectra (MS) were measured by electron-spray ion-mass spectroscopy.

A variety of chromatographic techniques may be employed in the preparation of the compounds. These techniques include, but are not limited to: High Performance Liquid Chromatography (HPLC) including normal phase, reversed phase, and chiral phase HPLC; Medium Pressure Liquid Chromatography (MPLC), Super Critical Fluid Chromatography; preparative Thin Layer Chromatography (prep TLC); flash chromatography with silica gel or reversed-phase silica gel; ion-exchange chromatography; and radial chromatography. All temperatures are degrees Celsius unless otherwise noted.

The phrase "standard peptide coupling reaction conditions" means coupling a carboxylic acid with an amine using an acid activating agent such as EDC, DCC, and BOP in an inert solvent such as dichloromethane in the presence of a catalyst such as HOBT and HOAT. The use of protecting groups for the amine and carboxylic acid functionalities to facilitate the desired reaction and minimize undesired reactions is well documented. Conditions required to remove protecting groups are found in standard textbooks such as Greene, T, and Wuts, P. G. M., *Protective Groups in Organic Synthesis*, John Wiley & Sons, Inc., New York, N.Y., 1991. MOZ and BOC are commonly used protecting groups in organic synthesis, and their removal conditions are known to those skilled in the art. For example, MOZ may be removed by catalytic hydrogenation in the presence of a noble metal or its oxide such as palladium on activated carbon in a protic solvent such as methanol or ethanol. In cases where catalytic hydrogenation is contraindicated due to the presence of other potentially reactive functionalities, removal of MOZ groups can also be achieved by treatment with a solution of trifluoroacetic acid, hydrochloric acid or hydrogen chloride gas, in a solvent such as dichloromethane, methanol, or ethyl acetate. Removal of BOC protecting groups is carried out with a strong acid, such as trifluoroacetic acid, hydrochloric acid, or hydrogen chloride gas, in a solvent such as dichloromethane, methanol, or ethyl acetate.

Throughout the application, the following terms have the indicated meanings unless noted otherwise:

| Term | Meaning |
|---|---|
| Ac | Acyl (CH$_3$C(O)—) |
| Aq. | Aqueous |
| Bn | Benzyl |
| BOC (Boc) | t-Butyloxycarbonyl |
| BOP | Benzotriazol-1-yloxytris(dimethylamino)phosphonium hexafluorophosphate |
| ° C. | Degree Celsius |
| Calc. or calc'd | Calculated |
| Celite | Celite$^{TM}$ diatomaceous earth |
| DCC | Dicyclohexylcarbodiimide |
| DCM | Dichloromethane |
| DIEA | N,N-diisopropyl-ethylamine |
| DMAP | 4-Dimethylaminopyridine |
| DMF | N,N-dimethylformamide |
| EDC | 1-Ethyl-3-(3-dimethylaminopropyl) carbodiimide |
| Eq. or equiv. | Equivalent(s) |
| ES-MS and ESI-MS | Electron spray ion-mass spectroscopy |
| Et | Ethyl |
| EtOAc | Ethyl acetate |
| g | Gram(s) |
| h or hr | Hour(s) |
| HATU | O-(7-azabenzotriazol-1-yl)-N,N,N,N'-tetramethyluronium hexafluorophosphate |
| HCl | Hydrogen chloride |
| HOAc | Acetic acid |
| HOAT | 1-Hydroxy-7-azabenzotriazole |
| HOBT | 1-Hydroxybenzotriazole |
| HPLC | High performance liquid chromatography |
| IPA | Isopropyl alcohol |
| kg | Kilogram(s) |
| LC/MS or LC-MASS | Liquid chromatography mass spectrum |
| L | Liter(s) |
| LDA | Lithium diisopropylamide |
| LiOH | Lithium hydroxide |
| LiHMDS | Lithium bis(trimethylsilyl)amide |
| M | Molar(s) |
| Me | Methyl |
| MeOH | Methanol |
| MF | Molecular formula |
| min | Minute(s) |
| mg | Milligram(s) |
| mL | Milliliter(s) |
| mmol | Millimole(s) |
| MOZ (Moz) | p-Methoxybenzyloxycarbonyl |
| MP | Melting point |
| MS | Mass spectrum |
| NaH | Sodium hydride |

| Term | Meaning |
| --- | --- |
| nM | Nanomolar |
| OTf | Trifluoromethanesulfonyl |
| 10% Pd/C | Palladium, 10 weight percent on activated carbon |
| Ph | Phenyl |
| Prep. | Preparative |
| Ref. | Reference |
| r.t. or rt or RT | RT |
| Sat. | Saturated |
| SCF $CO_2S$ | Super critical fluid carbon dioxide |
| TBAF | Tetrabutylammonium fluoride |
| TBAI | Tetrabutylammonium iodide |
| TBDPS | Tert-butyl diphenylsilyl |
| TBS, TBDMS | Tert-butyl dimethylsilyl |
| TEA or $Et_3N$ | Triethylamine |
| Tf | Triflate or trifluoromethanesulfonate |
| TFA | Trifluoroacetic acid |
| THF | Tetrahydrofuran |
| TLC | Thin-layer chromatography |
| TMS | Trimethylsilyl |
| TMSOK | Potassium trimethylsilanolate |

Reaction Schemes below illustrate the methods employed in the synthesis of the compounds described herein. All substituents are as defined above unless indicated otherwise. The synthesis of the novel compounds described herein may be accomplished by one or more of several similar routes. The Examples further illustrate details for the preparation of the compounds described herein. Those skilled in the art will readily understand that known variations of the conditions and processes of the following preparative procedures can be used to prepare these compounds. The instant compounds are generally isolated in the form of their pharmaceutically acceptable salts, such as those described previously hereinabove. The free amine bases corresponding to the isolated salts can be generated by neutralization with a suitable base, such as aqueous sodium hydrogen carbonate, sodium carbonate, sodium hydroxide, and potassium hydroxide, and extraction of the liberated amine free base into an organic solvent followed by evaporation. The amine free base isolated in this manner can be further converted into another pharmaceutically acceptable salt by dissolution in an organic solvent followed by addition of the appropriate acid and subsequent evaporation, precipitation, or crystallization. All temperatures are degrees Celsius unless noted otherwise. Mass spectra (MS) were measured by electron-spray ion-mass spectroscopy.

Scheme I

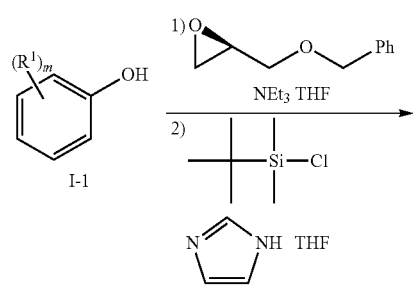

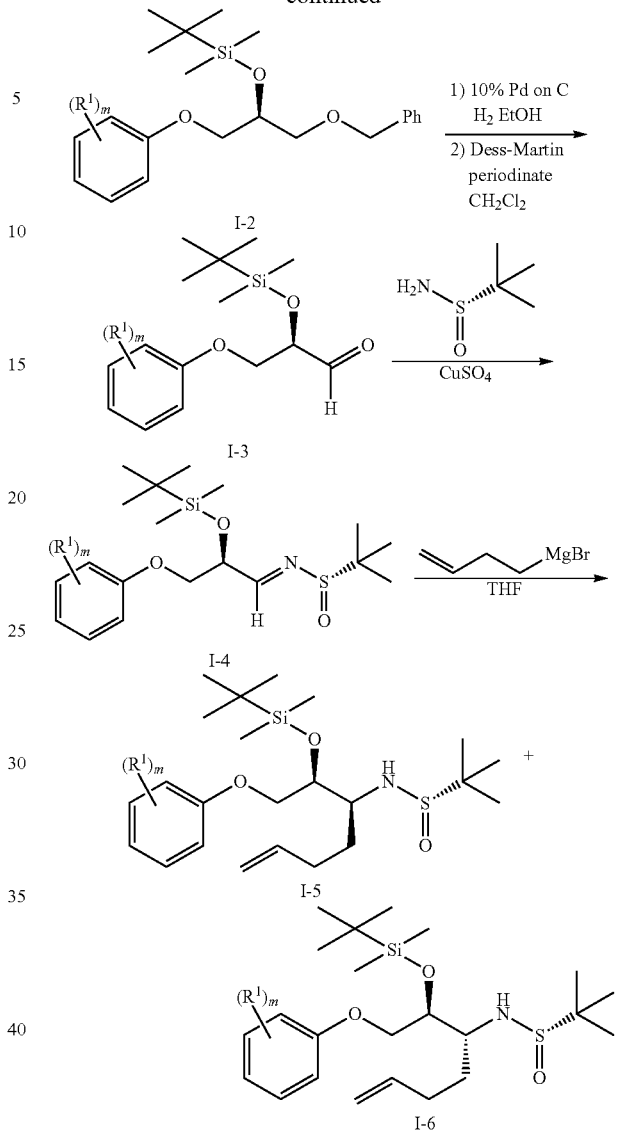

In Scheme I, an appropriately substituted phenol I-1 can be reacted with (R)-(−)-benzyl glycidyl ether in the presence of a catalytic amount of an organic base such as triethylamine at 40° C. for 12-18 h from which the epoxide ring-opened product may be obtained. This secondary alcohol product may be protected by adding tert-butyldimethylsilyl chloride in the presence of an organic base such as imidazole or trialkylamine at RT for 12-16 h to afford the silylated ether I-2. The reaction is usually performed in an inert organic solvent such as THF under an inert atmosphere such as nitrogen.

The benzyl group may then be removed. Treatment of silyl ether I-2 as an alcohol solution, for example ethyl alcohol, with hydrogen gas over a hydrogenation catalyst such as 10% palladium on carbon, at RT over a period of 2 h yields the primary alcohol. The alcohol may be converted to the aldehyde I-3 by an oxidation reaction with an oxidizing agent such as Dess-Martin periodinate in a chlorinated solvent such as methylene chloride. Conversion of the aldehyde to the sulfinylimine I-4 may be effected with (S)-tert-butylsulfinylamide in the presence of a dehydrating agent such as anhydrous copper(II) sulfate. The resulting amine can then be reacted with 3-butenylmagnesium bromide in THF or methylene chloride to afford a mixture of diastereomeric compounds I-5 and I-6 that may be separated by those skilled in the art of chromatography.

Scheme II below describes the synthesis of key acid scaffolds of the structural formula I-16 to which several beta-3 AR analogs can be synthesized. The vinyl intermediate I-6, acquired from the synthesis described in Scheme 1, may be reacted in an olefin cross metathesis with any substituted aromatic styrene, I-7, using appropriate catalysts useful in olefin metathesis known to those skilled in the art. Suitable catalysts include, but are not limited to, both "Grubbs" and "Zhan" catalysts and of the type known as Grubbs-II and Zhan I or II to produce the compound of structural formula I-8. Protection group manipulation on the nitrogen, known to those skilled in the art, affords intermediate 1-9 which then can be treated with an oxidizing reagent such as meta-chloroperbenzoic acid, m-CPBA, to afford the epoxide I-10.

The epoxide I-10 may then be hydrogenated with 10% palladium on carbon under high pressure hydrogen gas (40 PSI) to afford the alcohol with structural formula I-11. Oxidation of I-11 with an oxidizing reagent such as Dess-Martin affords the ketone I-12. After purification, the ketone may then be used to form the imine via deprotection of the amine in the presence of an acid such as TFA or HCl. During the deprotection, cyclization may immediately ensue to form imine I-13 which then should be used directly without purification to form the pyrrolidine I-14 by hydrogenation in the presence of 10% palladium on carbon in an alcoholic solvent such as methanol or ethanol. Protection of the amine with tert-butyl-dicarbonate ($Boc_2O$) in the presence of a suitable base such as DIEA or TEA affords the penultimate intermediate I-15. Saponification of the ester to the acid in the presence of an inorganic base such as LiOH or NaOH affords the desired acid intermediate with the structural formula I-16.

Scheme II

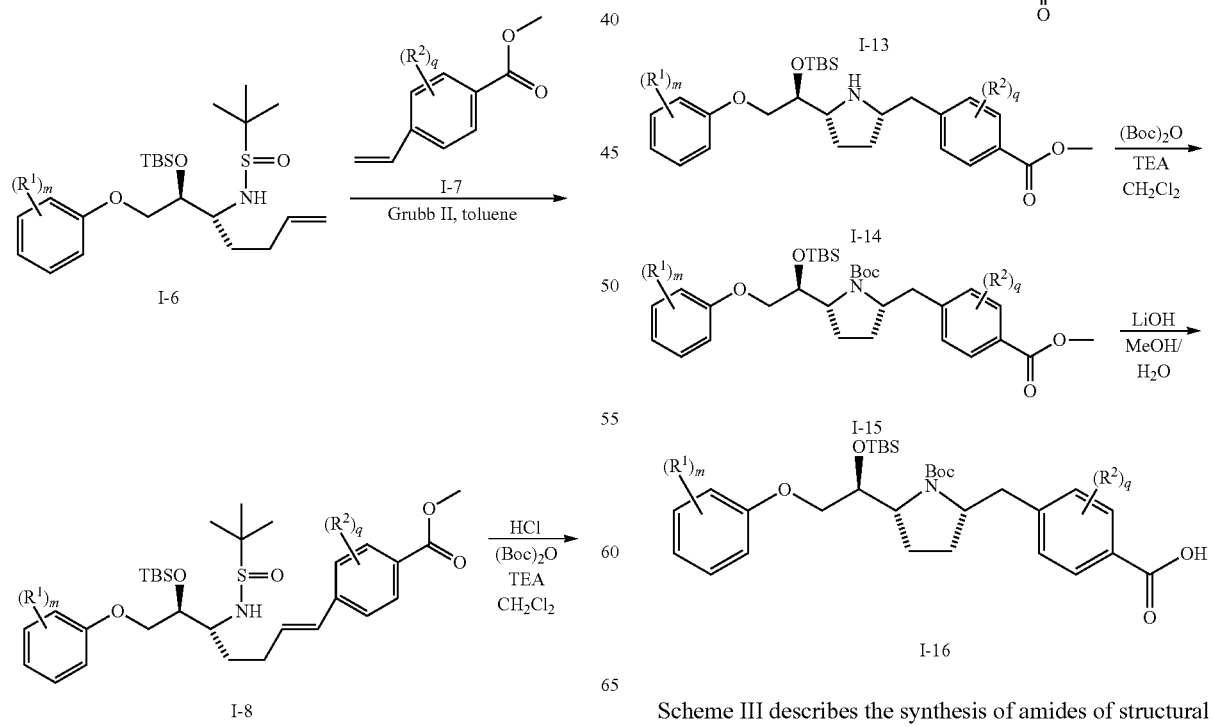

Scheme III describes the synthesis of amides of structural formula I-19 via appropriate amide bond formation conditions known to those skilled in the arts such as EDC, DCC, HATU or BOP in the presence of the appropriate additive such as HOAT or HOBT, and either with or without a suitable organic base, such as N,N-diisopropylethylamine or triethylamine. For example, a desired amine I-17 and pyrrolidine carboxylic acid I-16 can be treated with N-(3-dimethylaminopropyl)-N'-ethylcarbodiimide (EDC) hydrochloride and 1-hydroxybenzotriazole (HOBt) in the presence of a suitable organic base, such as N,N-diisopropylethylamine. The reaction is usually performed in an inert organic solvent such as N,N-dimethylformamide, at RT for a period of 2-24 h. Removal of the Boc protecting groups of I-18 via treatment with a solution of TFA in an inert organic solvent, such as dichloromethane, at ambient temperature for a period of time between 1 and 6 h affords the final desired products of various amides shown in the general structural formula I-19. Alternatively, treatment of I-18 with a solution of hydrogen chloride in an organic solvent, such as 1,4-dioxane or ethyl acetate, also yields the desired product of structural formula I-19.

Additional de-protection steps may be included if there are useful protecting groups known to those skilled in the art necessary to allow the chemistry to proceed in a facile fashion. These protecting groups may include trityl groups, benzylcarbamate groups, ester groups, silyl groups or other groups suitable for the protection of heterocyclic compounds or the functional groups such as amines, hydroxyls, carboxylic acids or other groups known to those skilled in the art.

Scheme III

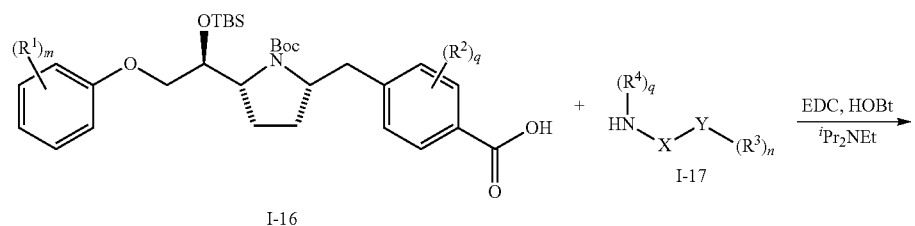

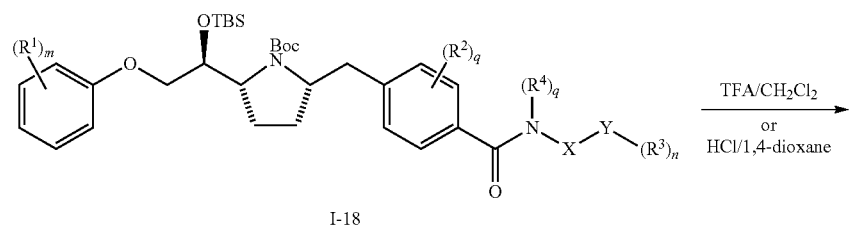

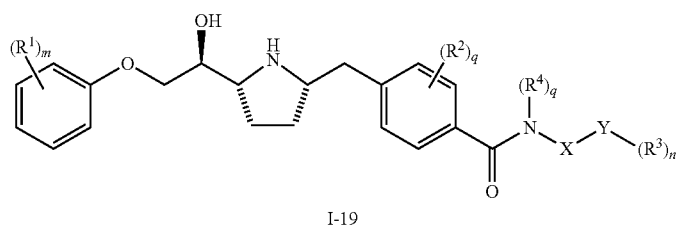

In some cases the order of carrying out the foregoing reaction schemes may be varied to facilitate the reaction or to avoid unwanted reaction products. The following examples are provided so that the invention might be more fully understood. These examples are illustrative only and should not be construed as limiting the invention in any way.

INTERMEDIATE 1-2

N-[(1R)-1-((1S)-1-{[tert-butyl(dimethyl)silyl]oxy}-2-phenoxyethyl)pent-4-en-1-yl]-2-methylpropane-2-sulfinamide (i-1) and N-[(1S)-1-((1S)-1-{[tert-butyl(dimethyl)silyl]oxy}-2-phenoxyethyl)pent-4-en-1-yl] 2-methylpropane-2-sulfinamide (i-2)

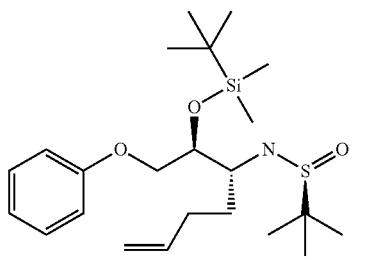

(i-1)

and

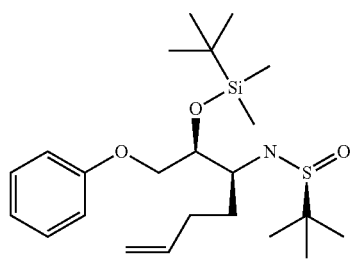

(i-2)

Step A: (2S)-1-(benzyloxy)-3-phenoxypropan-2-ol

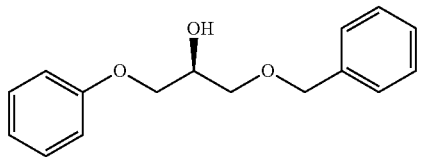 [SMILES: O[C@@H](COCc1ccccc1)COc1ccccc1]

A solution of phenol (3.3 g; 35 mmol), benzyl (R)-(+)-glycidyl ether (5 g; 30.5 mmol) and triethylamine (300 µl; 2.15 mmol) in absolute ethanol (80 ml) was heated to reflux and stirred for 2 h and then cooled to 60° C. and stirred overnight. The crude reaction mixture was concentrated under reduced pressure and the residues purified by silica gel chromatography using an eluant of hexanes and ethyl acetate (85:15 v/v) to afford 5.7 g (72.5%) of the pure product. m/z (ES) 281.1 (M+Na)$^+$.

Step B: [(1S)-2-(benzyloxy)-1-(phenoxymethyl)ethoxy](tert-butyl)dimethylsilane

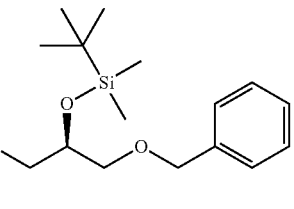

The alcohol (5.4 mg; 20.9 mmol) from Step A in methylene chloride (100 ml) was stirred at 0° C. Triethylamine (3.5 ml; 25.1 mmol) was added to the solution and followed with t-butyldimethylsilyl trifluoromethanesulfonate (5.8 g; 21.95 mmol). The reaction mixture was stirred at 0° C. for 1 h, then quenched by the addition of saturated aqueous sodium bicarbonate solution and washed with water and brine. The organic phase was separated and concentrated to give approximately 10 gram of crude material that was purified by silica gel chromatography using an eluant of hexane and ethyl acetate (95:5 v/v). A 7.4 g yield of the silylated product was obtained. m/z (ES) 373 (M+H)$^+$ and 395 (M+Na)$^+$ Step C: (2S)-2-{[tert-butyl(dimethyl)silyl]oxy}-3-phenoxypropan-1-ol

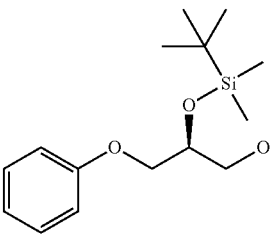

To the silyl-ether (7.2 g; 19.33 mmol) from Step B in ethanol (100 ml) as prepared was added 10% palladium on carbon (700 mg). The resulting reaction mixture was hydrogenated at room temperature at 40 psi for 16 h on a Parr hydrogenator. The spent catalyst was removed by filtration and the filtrate thus obtained was concentrated under reduced pressure to afford the crude product. Purification of the crude product by silica gel chromatography using an eluant of hexanes and ethyl acetate (9:1 v/v) gave 4.85 g (89%) yield of the desired primary alcohol product. m/z (ES) 305 (M+Na)+.

Step D: (2R)-2-{[tert-butyl(dimethyl)silyl]oxy}-3-phenoxypropanal

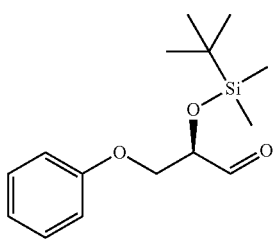 [SMILES: CC(C)(C)[Si](C)(C)O[C@@H](CO)COc1ccccc1]

A solution of the primary alcohol (2.4 g; 8.5 mmol) from Step C above and Dess-Martin periodinate reagent (4.14 g; 9.77 mmol) in anhydrous methylene chloride (80 ml) was stirred at RT for 2 h. The reaction was quenched with saturated aqueous sodium bicarbonate solution and then extracted with methylene chloride (3×60 ml). The combined methylene chloride extracts were dried over anhydrous sodium sulfate, filtered through a pad of silica gel and the filtrates thus obtained concentrated under reduced pressure to give 2.22 g (93%) of crude product that had sufficient purity for use in Step E. This procedure was repeated with the rest of the alcohol to give another 2.08 grams of the aldehyde product.

Step E: (S)—N-((1E,2S)-2-{[tert-butyl(dimethyl)silyl]oxy}-3-phenoxypropylidene)-2-methylpropane-2-sulfinamide

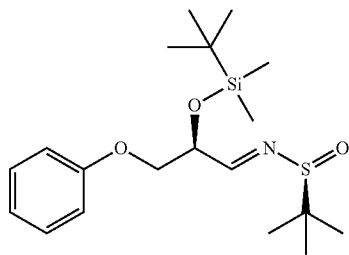 [SMILES: CC(C)(C)[S@](=O)/N=C/[C@@H](COc1ccccc1)O[Si](C)(C)C(C)(C)C]

Under a nitrogen inert atmosphere, a solution of the aldehyde (3.80 g; 13.55 mmol) from Step D and (S)-(−)-2-methyl-2-propanesulfinamide (4.10 g; 33.88 mmol) in methylene chloride (100 ml) was stirred at RT and to this solution anhydrous copper sulfate powder (4.50 g; 28.21 mmol) was added. The reaction mixture was stirred at ambient temperature overnight. The reaction was quenched with water and the two layers separated. The methylene chloride phase was dried over sodium sulfate, filtered and then concentrated under reduced pressure to afford 4.58 g of the crude reaction product that used in Step F described below. m/z (ES) 384.5 (M+H)+.

Step F: N-[(1R)-1-((1S)-1-{[tert-butyl(dimethyl)silyl]oxy}-2-phenoxyethyl)pent-4-en-1-yl]-2-methylpropane-2-sulfinamide (i-1) and N-[(1S)-1-((1S)-1-{[tert-butyl(dimethyl)silyl]oxy}-2-phenoxyethyl)pent-4-en-1-yl]2-methylpropane-2-sulfinamide (i-2)

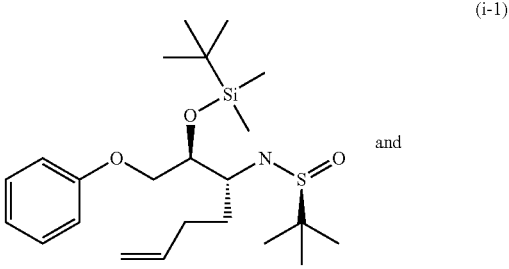

and

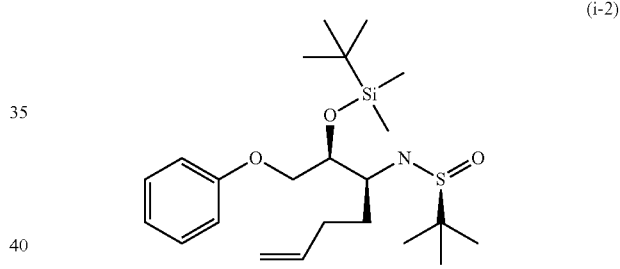

A solution of the sulfinamide (4.00 g; 10.43 mmol) from Step E in anhydrous methylene chloride (100 ml) was stirred at RT and to this solution 3-butenylmagnesium bromide in THF (0.5 M) (42 ml; 21.00 mmol) was added drop by drop. The resulting reaction mixture stirred at RT for 1.5 h and then the reaction mixture was quenched with saturated aqueous ammonium chloride solution and extracted with methylene chloride (3×200 ml). The methylene chloride extracts were combined and washed with brine and then dried over anhydrous sodium sulfate powder, filtered and concentrated under reduced pressure. The crude product (approx. 3.50 g) that was obtained on evaporation was purified by flash column (silica gel) eluted with hexanes and ethyl acetate (2:1 v/v). Two product containing bands (TLC reference: $R_f$~0.55 and 0.4) were isolated. The band related to the TLC reference of $R_f$~0.4 afforded 1.75 g of N-[(1R)-1-((1S)-1-{[tert-butyl (dimethyl)silyl]oxy}-2-phenoxyethyl)pent-4-en-1-yl]-2-methylpropane-2-sulfinamide (i-1). m/z (ES) 440.2 (M+H)+

The band with TLC reference of $R_f$~0.55 yielded an impure product that was re-purified by preparative TLC on silica gel plates (20 cm×20 cm×1000 microns) eluted with hexanes, ethyl acetate, and methylene chloride (3:1:1) from which 310 mg of N-[(1S)-1-((1S)-1-{[tert-butyl(dimethyl)silyl]oxy}-2-phenoxyethyl)pent-4-en-1-yl]-2-methylpropane-2-sulfinamide (i-2) was obtained along with 220 mg of an unidentified impurity. m/z (ES) 440.2 (M+H)+.

INTERMEDIATE 3

4-{[(2S,5R)-1-(tert-butoxycarbonyl)-5-((1S)-{[tert-butyl(dimethyl)silyl]oxy}-2-phenoxyethyl) pyrrolidin-2-yl]methyl}benzoic acid

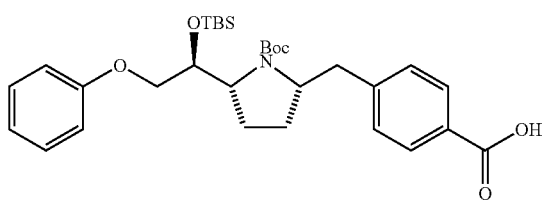

Step A: methyl 4-{(1E,5R,6S)-6-{[tert-butyl(dimethyl)silyl]oxy}-5-[(tert-butylsulfinyl)amino]-7-phenoxyhept-1-en-1-yl}benzoate

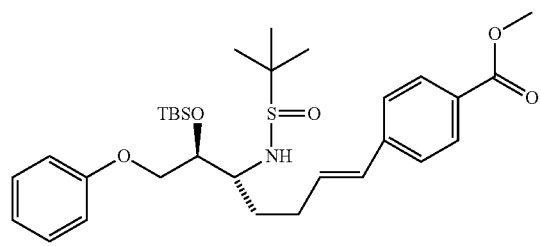 [SMILES: COC(=O)c1ccc(/C=C/CC[C@@H](NS(=O)C(C)(C)C)[C@@H](COc2ccccc2)O[Si](C)(C)C(C)(C)C)cc1]

To a solution of olefin, i-1, (5.3 g, 12.28 mM) and methyl 4-vinylbenzoate (3.98 g, 24.56 mM) in 80 ml of anhydrous methylene chloride, purged with nitrogen gas for 10 min, was added GrubbII catalyst (0.42 g, 0.49 mM), and the resulting mixture was stirred for 40 h under nitrogen at RT. Filtered through a celite pad and the filtrate was concentrated in vacuo. The residue was loaded onto a Biotage column (65i) eluting with hexane/ethyl acetate (EA) (0-20% EA 500 ml, 20-70% EA, 1000 ml, 70-100% EA, 600 ml) to give 2.4 g of the title compound. LC-MS: m/z (ES) 574.31 (M+1).

Step B: methyl 4-{(1E,5R,6S)-5-amino-6-{[tert-butyl(dimethyl)silyl]oxy}-7-phenoxyhept-1-en-1-yl}benzoate

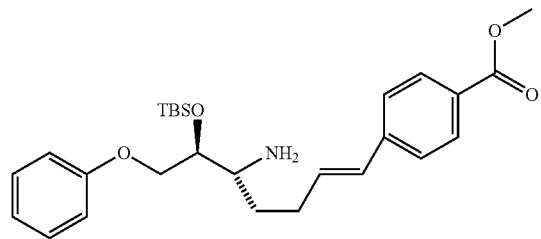 [SMILES: COC(=O)c1ccc(/C=C/CC[C@@H](N)[C@@H](COc2ccccc2)O[Si](C)(C)C(C)(C)C)cc1]

To the solution of methyl 4-{(1E,5R,6S)-6-{[tert-butyl(dimethyl)silyl]oxy}-5-[(tert-butylsulfinyl)amino]-7-phenoxyhept-1-en-1-yl}benzoate from step A (1.05 g, 1.74 mM) in 10 ml of methylene chloride was added 1 ml of HCl (4M, in dioxane) and the resulting mixture stirred at RT for 15 min. Removal of the volatiles under reduced pressure afforded 0.93 g of the title compound (as HCl salt) which was directly used for the next step. LC-MS: m/z (ES) 470.41 (M+1).

Step C: methyl 4-{(1E,5R,6S)-5-[(tert-butoxycarbonyl)amino]-6-{[tert-butyl(dimethyl)silyl]oxy}-7-phenoxyhept-1-en-1-yl}benzoate

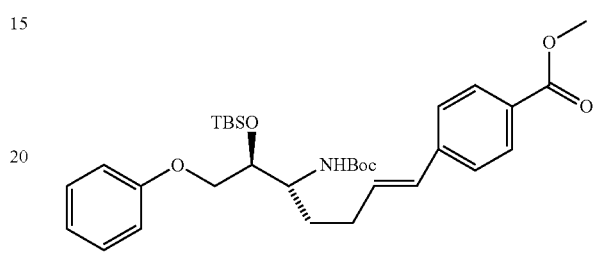

To a solution of methyl 4-{(1E,5R,6S)-5-amino-6-{[tert-butyl(dimethyl)silyl]oxy}-7-phenoxyhept-1-en-1-yl}benzoate from step B (0.93 g, 1.83 mM) and DIEA (0.47 g, 3.7 mM) in 15 ml of methylene chloride was added di-tert-butyl dicarbonate (Boc2O) (0.48 g, 2.2 mM) and the resulting mixture was stirred for 16 h. All volatiles were removed under reduced pressure and the residue was partitioned between saturated aqueous sodium bicarbonate solution and ethyl acetate, separated, and organic layer washed by brine, concentrated in vacuo. The residue was then loaded on Biotage column eluting with hexane/ethyl acetate (EA) (0-20% EA, 400 ml; 20-30% EA, 400 ml; 30-100% EA, 200 ml) to give 665 mg of the title compound. LC-MS: m/z (ES) 570.29 (M+1).

Step D: methyl 4-[3-((3R,4S)-3-[(tert-butoxycarbonyl)amino]-4-{[tert-butyl(dimethyl)silyl]oxy}-5-phenoxypentyl)oxiran-2-yl]benzoate

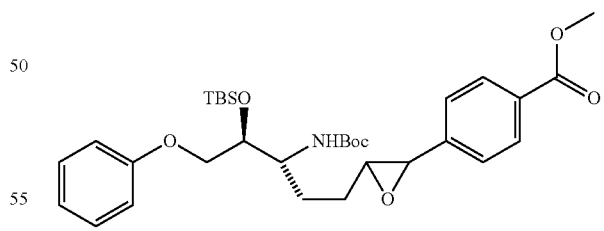

To the solution of methyl 4-{(1E,5R,6S)-5-[(tert-butoxycarbonyl)amino]-6-{[tert-butyl(dimethyl) silyl]oxy}-7-phenoxyhept-1-en-1-yl}benzoate from step C (405 mg, 0.71 mM) in 15 ml of methylene chloride was added m-CBPA (226 mg, 0.85 mM) and the reaction was left stirring overnight at RT. Volatiles were removed in vacuo and the residue was partitioned between saturated aqueous sodium bicarbonate solution and ethyl acetate, separated, dried over sodium sulfate, filtered and concentrated under reduced pressure to afford 415 mg of the title compound. This material was directly used for next step. LC-MS: m/z (ES) 486.17 (M-Boc+1).

Step E: methyl 4-{(5R,6S)-5-[(tert-butoxycarbonyl)amino]-6-{[tert-butyl(dimethyl)silyl]oxy}-2-hydroxy-7-phenoxyheptyl}benzoate

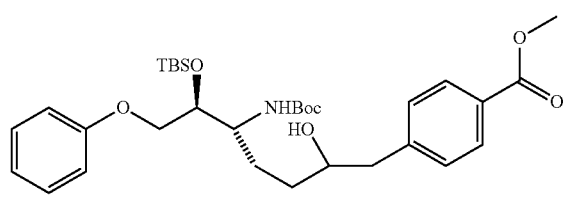 [SMILES: COC(=O)c1ccc(CC(O)CC[C@@H](NC(=O)OC(C)(C)C)[C@@H](COc2ccccc2)O[Si](C)(C)C(C)(C)C)cc1]

To a solution of methyl 4-[3-((3R,4S)-3-[(tert-butoxycarbonyl)amino]-4-{[tert-butyl(dimethyl)silyl]oxy}-5-phenoxypentyl)oxiran-2-yl]benzoate from step D (410 mg, 0.7 mM) in 15 ml of methanol was added 100 mg of palladium on carbon (10%) and the suspension was set under 40 PSI of hydrogen gas and shaken for 2 h on the Parr shaker. The catalyst was filtered and the filtrate concentrated under reduced pressure to afford 378 mg of the title compound which was directly used for next step. LC-MS: m/z (ES) 488.21 (M-Boc+1).

Step F: methyl 4-{(5R,6S)-5-[(tert-butoxycarbonyl)amino]-6-{[tert-butyl(dimethyl)silyl]oxy}-2-oxo-7-phenoxyheptyl}benzoate

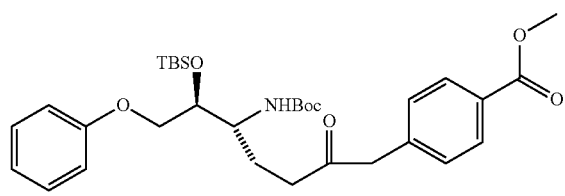 [SMILES: COC(=O)c1ccc(CC(=O)CC[C@@H](NC(=O)OC(C)(C)C)[C@@H](COc2ccccc2)O[Si](C)(C)C(C)(C)C)cc1]

Dess-martin reagent (390 mg, 0.92 mM) was placed in a 100 ml round bottom flask and 5 ml of methylene chloride was added, 5 min later, methyl 4-{(5R,6S)-5-[(tert-butoxycarbonyl)amino]-6-{[tert-butyl(dimethyl)silyl]oxy}-2-hydroxy-7-phenoxyheptyl}benzoate from step E (360 mg, 0.61 mM) in 5 ml of methylene chloride was added, and the resulting mixture was stirred for 3 h at RT. The mixture was then filtered and the filtrate was washed by saturated aqueous sodium bicarbonate solution, dried over sodium sulfate and concentrated to dryness. The residue was then loaded onto a Biotage column (40 S) and eluted with hexane/ethyl acetate (0-30% EA, 500 ml; 30-50% EA, 300 ml) to afford 139 mg of the title compound. LC-MS: m/z (ES) 608.24 (M=23).

Step G: methyl 4-{[(2R)-2-((1S)-1-{[tert-butyl(dimethyl)silyl]oxy}-2-phenoxyethyl)-3,4-dihydro-2H-pyrrol-5-yl]methyl}benzoate

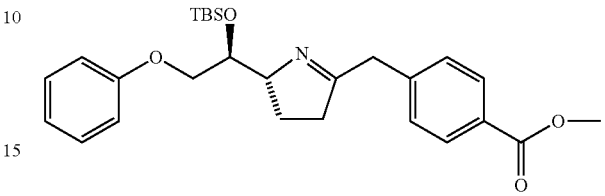

Methyl 4-{(5R,6S)-5-[(tert-butoxycarbonyl)amino]-6-{[tert-butyl(dimethyl)silyl]oxy}-2-oxo-7-phenoxyheptyl}benzoate from step F (130 mg, 0.22 mM) in 5 ml of methylene chloride was treated with 0.5 ml of TEA at RT for 20 min. The volitiles were removed via concentrating under reduced pressure to afford 129 mg of the title compound. This material was directly used for next step. LC-MS: m/z (ES) 468.17 (M+1).

Step H: methyl 4-{[(2S,5R)-5-((1S)-1-{[tert-butyl(dimethyl)silyl]oxy}-2-phenoxyethyl)-2-pyrrolidin-2-yl]methyl}benzoate

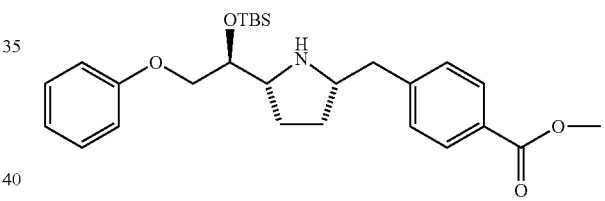

To a solution of methyl 4-{[(2R)-2-((1S)-1-{[tert-butyl(dimethyl)silyl]oxy}-2-phenoxyethyl)-3,4-dihydro-2H-pyrrol-5-yl]methyl}benzoate from step G (118 mg, 0.2 mM) 10 ml of methanol was added 140 mg of palladium on carbon (10%) and the resulting suspension was stirred under a balloon of hydrogen gas for 4 h. The catalyst was filtered off and the filtrate was concentrated in vacuo to afford 134 mg of the title compound which was directly used for next step. LC-MS: m/z (ES) 470.22 (M+1).

Step I: tert-butyl (2R,5S)-2-((1S)-1-{[tert-butyl(dimethyl)silyl]oxy}-2-phenoxyethyl)-5-[4-(methoxycarbonyl)benzyl]pyrrolidine-1-carboxylate

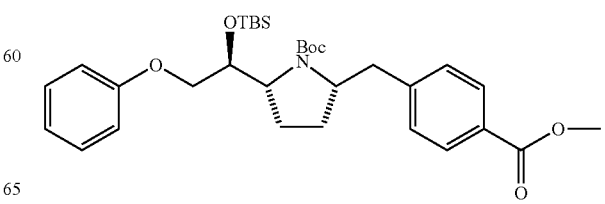

To the solution of methyl 4-{[(2S,5R)-5-((1S)-1-{[tert-butyl(dimethyl)silyl]oxy}-2-phenoxyethyl)-pyrrolidin-2-yl]methyl}benzoate from step H (130 mg, 0.28 mM) and 0.12 ml of triethylamine in 4 ml of methylene chloride was added di-tert-butyl dicarbonate (Boc$_2$O) (70 mg, 0.32 mM) and the resulting mixture was stirred for 2 h at RT. All volatiles were removed under reduced pressure and the residue was purified on 2 preparative TLC plates (1000 μM) using 20% ethyl acetate in hexane to afford 75 mg of the title compound. LC-MS: m/z (ES) 470.21 (M-Boc+1), 592.33 (M+23).

Step J: 4-{[2S,5R)-1-(tert-butoxycarbonyl)-5-((1S)-1-{[tert-butyl(dimethyl)silyl]oxy}-2-phenoxyethyl)pyrrolidin-2-yl]methyl}benzoic acid

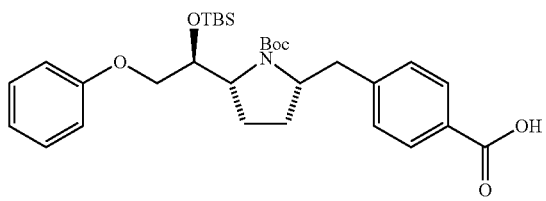

To the solution of tert-butyl (2R,5S)-2-((1S)-1-{[tert-butyl(dimethyl)silyl]oxy}-2-phenoxyethyl)-5-[4-(methoxycarbonyl)benzyl]pyrrolidine-1-carboxylate from step I (75 mg, 0.13 mM) in 3 ml of methanol was added 0.26 ml of aqueous lithium hydroxide (LiOH) (1.0M, 0.26 mM), stirred at 45° C. for 1 h, then 0.13 ml more of LiOH (1.0 M)) was added and stirred at 65° C. for 40 min, then 30° C. for overnight. The reaction solution was then neutralized by addition of 0.38 ml of HCl aqueous solution (1 M), removal of the volatiles in vacuo afforded 91 mg of title compound. LC-MS: m/z (ES) 456.20 (M-Boc+1).

INTERMEDIATE 4

4-(1H-pyrazol-1-yl)piperidine (i-4)

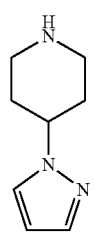

(i-4)

Step A: tert-butyl 4-[(methylsulfonyl)oxy]piperidine-1-carboxylate

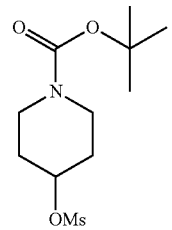 [SMILES: CC(C)(C)OC(=O)N1CCC(OS(C)(=O)=O)CC1]

To a solution of tert-butyl 4-hydroxypiperidine-1-carboxylate (550 mg, 2.5 mmol) and DMAP (296 mg, 2.5 mmol) in dichloromethane (15 mL) cooled to 0° C. by ice/water bath was added methanesulfonylchloride (189 μL, 2.5 mmol) and the resulting mixture stirred for 10 min at 0° C. and then for an additional hour at RT. The mixture was quenched with ice water and extracted with ethyl acetate (2×30 mL). The organic layer was washed with water and brine, dried over sodium sulfate, filtered and concentrated under vacuum. The residue oil was purified via silica gel preparative plates (3×1000 mM) eluting with 50% ethyl acetate in hexane to afford the title compound (555 mg, 89%). EST-MS calculated for $C_{11}H_{21}NO_5S$: Exact Mass: 279.11. Found 302.13 (MNa)$^+$.

Step B: tert-butyl 4-(1H-pyrazol-1-yl)piperidine-1-carboxylate

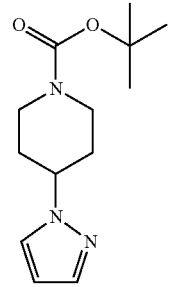 [SMILES: CC(C)(C)OC(=O)N1CCC(n2cccn2)CC1]

To a solution of pyrazole (100 mg, 1.50 mmol) in DMF (10.0 ml) under nitrogen atmosphere was added sodium hydride (60 mg, 1.65 mmol) and the solution stirred for 5 min. After bubbling ceased, the title compound from Step A (204 mg, 1.50 mmol) in 2.5 mL of DMF was added to the solution. The mixture was placed in a microwave reaction vessel and nitrogen was blown into it before closing.

Microwave: The reaction was set at 150° C. for 15 minutes on high absorption. After the reaction cooled, it was quenched with ammonium chloride solution and extracted with ethyl acetate. The organic layer was dried over sodium sulfate, filtered and concentrated to dryness. Purification of the residue was done on silica gel preparative plate (500 μM) eluting with 70% ethyl acetate in hexane to afford the product (52.2 mg, 55%). ESI-MS calculated for $C_{13}H_{21}N_3O$: Exact Mass: 251.16. Found: 252.16 (MH)$^+$ and 274.15 (MNa)$^+$.

Step C: 4-(1H-pyrazol-1-yl)piperidine (i-4)

The title compound from Step B above (50 mg, 0.2 mmol) was dissolved in 4 M HCl in dioxane (2.0 mL) and stirred at RT for 1 h. The product was concentrated under reduced pressure and dried under high vacuum to give the title compound (i-17) (30 mg, 96%). ESI-MS calculated for $C_8H_{13}N_3$: Exact Mass: 151.11. Found 152.10.

INTERMEDIATES 5-6 (i-5-i-6)

The following N-heterocyclic substituted piperidine intermediates were prepared from the appropriate starting materials using the procedures described above and procedures known in the art.

TABLE 1

| Intermediate # | Structure | Calc. Mass | MS (e/z) (MH)+ |
|---|---|---|---|
| i-5 | 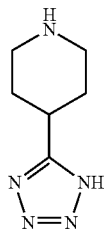 | 152.11 | 153.10 |
| i-6 | 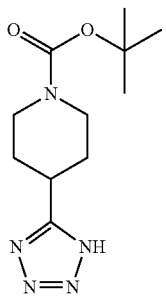 [SMILES: CC(C)(C)OC(=O)N1CCC(c2nnn[nH]2)CC1] | 152.11 | 153.10 |

INTERMEDIATE 7

4-(1H-tetrazol-5-yl)piperidine (i-7)

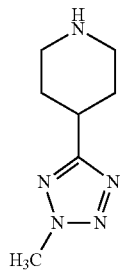

(i-7)

Step A: tert-butyl 4-(1H-tetrazol-5-yl)piperidine-1-carboxylate

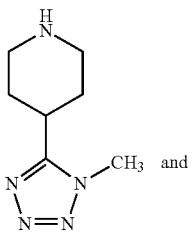

Sodium azide (228 mg, 3.50 mmol) was added to a stirred, cooled RT mixture of tert-butyl 4-cyanopiperidine-1-carboxylate (243 mg, 1.167 mmol) in DMF (5 ml) and the mixture was stirred at 100° C. for 48 h. The mixture was cooled, diluted with ethyl acetate (100 mL), washed with brine (3×50 mL), dried over sodium sulfate, filtered, and the solvent was evaporated under reduced pressure. The residue was purified by column chromatography on silica gel Biotage 40S, eluting with 10% methanol in dichloromethane to afford the title compound (197 mg, 75%) as a colorless liquid. ESI-MS calculated for $C_{11}H_{19}N_5O_2$: Exact Mass: 253.13. Found 254.12

Step B: 4-(1H-tetrazol-5-yl)piperidine (i-7)

The title compound from Step A above (197 mg, 0.77 mmol) was dissolved in 4 M HCl in dioxane (3.0 mL) and stirred at RT for 1 h. The product was concentrated under reduced pressure and dried under high vacuum to give the title compound (i-32) (116 mg, 98%). ESI-MS calculated for $C_6H_{11}N_5$: Exact Mass: 153.13. Found 154.12.

INTERMEDIATE 8 and 9

4-(1-methyl-1H-tetrazol-5-yl)piperidine (i-8) and 4-(2-methyl-2H-tetrazol-5-yl)piperidine (i-9)

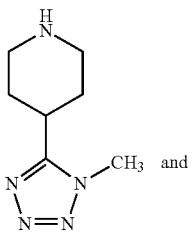

(i-8)

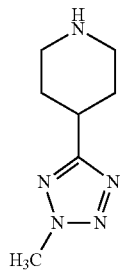

(i-9)

Step A: tert-butyl 4-(1-methyl-1H-tetrazol-5-yl)piperidine-1-carboxylate and tert-butyl 4-(2-methyl-2H-tetrazol-5-yl)piperidine-1-carboxylate

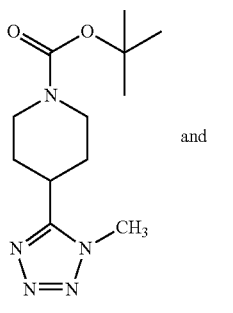 and 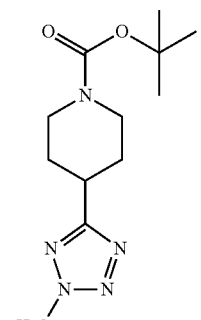

To a solution of tert-butyl 4-(1H-tetrazol-5-yl)piperidine-1-carboxylate (i-7, 100 mg, 0.4 mmol) and iodomethane (174 μL, 1.2 mmol) in anhydrous DMF (3 ml) was added cesium carbonate (800 mg, 2.4 mmol) and the resulting mixture heated to 80° C. for 2 h. After allowing to cool to RT, the mixture was poured into water and extracted with ethyl acetate (3×10 mL). The organics were combined, dried over magnesium sulfate, filtered and concentrated under reduced pressure. The residue was purified via preparative TLC plate (1000 μM) eluting with 80% ethyl acetate in hexane which also separate the two isomers. The isomers were labeled as isomer 1 and isomer 2 in the order that they eluted off the plate. Isomer 1 (45 mg, 25%) was identified as the Boc-4-(1-methyl-1H-tetrazol-5-yl) piperidine and the other (isomer 2, 30 mg, 16%) to be the 2-methyl substituted tetrazole.

Isomer 1: ESI-MS calculated for $C_{12}H_{23}N_5O_2$: Exact Mass: 267.13. Found 268.12

Isomer 2: ESI-MS calculated for $C_{12}H_{23}N_5O_2$: Exact Mass: 267.13. Found 268.12

Step B: 4-(1-methyl-1H-tetrazol-5-yl)piperidine (i-8)

The isomer 1 from Step A above (45 mg, 0.16 mmol) was dissolved in 4 M HCl in dioxane (1.0 mL) and stirred at RT for 1 h. The product was concentrated under reduced pressure and dried under high vacuum to give the title compound (i-8) (25 mg, 95%). ESI-MS calculated for $C_7H_{15}N_5$: Exact Mass: 167.13. Found 168.12.

Step C: 4-(2-methyl-2H-tetrazol-5-yl)piperidine (i-9)

The title compound (i-9) was prepared according to the procedure outlined above in Step B replacing the isomer 1 with the isomer 2 from Step A above.

ESI-MS calculated for both is $C_9H_{17}N_5$: Exact Mass: 167.13. Found 168.12.

INTERMEDIATE 10

6-(1H-tetrazol-1-yl)-3-azabicyclo[3.1.0]hexane (i-10)

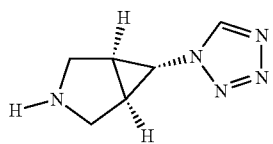

Step A: tert-butyl 6-(1H-tetrazol-1-yl)-3-azabicyclo[3.1.0]hexane-3-carboxylate

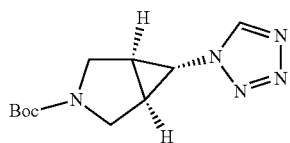 [SMILES: CC(C)(C)OC(=O)N1C[C@@H]2[C@H](C1)[C@H]2n1cnnn1]

To a solution of tert-butyl 6-amino-3-azabicyclo[3.1.0]hexane-3-carboxylate (7.3 g, 25.3 mmol) and triethylorthoformate (24 mL, 152 mmol) in acetic acid (200 mL) was added sodium azide (9.9 g, 152 mmol) and the resulting mixture was set under inert atmosphere. The mixture was heated at 100° C. for 4 h and then cooled to RT at which time the volatiles were removed in vacuo. The residue was taken up in ethyl acetate (200 mL) and washed with aqueous sodium bicarbonate solution, followed by brine. The organics were dried over sodium sulfate, filtered, and concentrate to dryness under vacuum. The residue was placed in the refrigerator overnight and the next day a solid white precipitate was observed. The precipitate was triturated with hexane and the solvent was carefully decanted to give the title compound 3.2 g (50.3%) as a white solid. ESI-MS calculated for $C_{11}H_{17}N_5O_2$: Exact Mass: 251.28. Found 252.28.

Step B: 6-(1H-tetrazol-1-yl)-3-azabicyclo[3.1.0]hexane (i-10)

The title compound from Step A above (2.6 g, 12.2 mmol) was dissolved in 4 M HCl in dioxane (200 mL) and stirred at RT overnight. The product was concentrated under reduced pressure and dried under high vacuum to give 6-(1H-tetrazol-1-yl)-3-azabicyclo[3.1.0]hexane. ESI-MS calculated for $C_6H_9N_5$: Exact Mass: 151.09. Found 152.05.

INTERMEDIATE 11

4-(Piperazin-1-ylmethyl)pyrimidine (i-11)

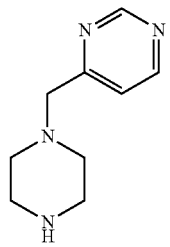

Step A: Benzyl 4-(pyrimidin-4-yl-methyl)piperazine-1-carboxylate

To a stirred solution of 0.20 g (1.8 mmol) of 1-(pyrimidin-4-yl)methanamine and 0.61 g (2.2 mmol) benzyl bis(2-chloroethyl)carbamate in 4 mL anhydrous diethylene glycol dimethyl ether was added 3.20 mL (18.3 mmol) of N,N-diisopropylethylamine and 0.05 g (0.40 mmol) of sodium iodide. The resulting solution was heated to 150° C. for 6 h. After cooling to ambient temperature, 12 mL of methanol was added to the mixture followed by 250 mL of diethyl ether. The resulting white precipitate was isolated by vacuum filtration while washing with diethyl ether. Diluted the solid with 100 mL of saturated sodium bicarbonate and extracted the aqueous solution with ethyl acetate (3×100 mL). The combined organic layers were dried with magnesium sulfate, filtered, and concentrated in vacuo to afford the title compound as a white solid which was used without further purification. LC/MS: m/z (ES) 313.1 (MH)⁺.

Step B: 4-(piperazin-1-ylmethyl)pyrimidine (i-11)

To 0.01 g (0.09 mmol) of 10% palladium on carbon was added a solution of 0.14 g (0.45 mmol) of the title compound from Step A in 5 mL anhydrous methanol. The resulting suspension was subjected to hydrogen at atmospheric pressure while stirring. After 4 h the mixture was filtered through a pad of Celite. The pad was washed with methanol (25 mL) and the combined filtrates were concentrated in vacuo to afford the title compound as a pale yellow residue without further purification. LC/MS: m/z (ES) 179.1 (MH)+.

Biological Assays: The following in vitro assays are suitable for screening compounds that have selective β3 agonist activity:

Functional Assay: cAMP production in response to ligand is measured according to Barton, et al. (1991, Agonist-induced desensitization of D2 dopamine receptors in human Y-79 retinoblastoma cells. Mol. Pharmacol. v3229:650-658) modified as follows. cAMP production is measured using a homogenous time-resolved fluorescence resonance energy transfer immunoassay (LANCE™, Perkin Elmer) according to the manufacture's instructions. Chinese hamster ovary (CHO) cells, stably transfected with the cloned β-adrenergic receptor (β1, β2 or β3) are harvested after 3 days of subculturing. Harvesting of cells is done with Enzyme-free Dissociation Media (Specialty Media). Cells are then counted and resuspended in assay buffer (Hank's Balanced salt solution supplemented with 5 mM HEPES, 01% BSA) containing a phosphodiesterase inhibitor (IBMX, 0.6 mM). The reaction is initiated by mixing 6,000 cells in 6 μL with 6 μL Alexa Fluor labeled cAMP antibody (LANCE™ kit) which is then added to an assay well containing 12 μL of compound (diluted in assay buffer to 2× final concentration). The reaction proceeds for 30 minutes at RT and is terminated by the addition of 24 ul detection buffer (LANCE™ kit). The assay plate is then incubated for 1 h at RT and time-resolved fluorescence measured on a Perkin Elmer Envision reader or equivalent. The unknown cAMP level is determined by comparing fluorescence levels to a cAMP standard curve.

The non-selective, full agonist 13-adrenergic ligand isoproterenol is used at all three receptors to determine maximal stimulation. The human β3 adrenergic receptor (AR) selective ligand (S)—N-[4-[2-[[2-hydroxy-3-(4-hydroxyphenoxy)propyl]amino]ethyl]-phenyl]-4-iodobenzenesulfonamide is used as a control in all assays. Isoproterenol is titrated at a final concentration in the assay of 10-10 M to 10-5 and the selective ligand (S)—N-[4-[2-[[2-hydroxy-3-(4-hydroxyphenoxy)propyl]amino]ethyl]phenyl]-4-iodobenzenesulfonamide is titrated at the β3 receptor at concentration of 10-10 M to 10-5 M. Unknown ligands are titrated at all 3 β-adrenergic receptor subtypes at a final concentration in the assay of 10-10 M to 10-5 M to determine the $EC_{50}$. The $EC_{50}$ is defined as the concentration of compound that gives 50% activation of its own maximum. Data are analyzed using Microsoft Excel and Graphpad Prism or an internally developed data analysis software package.

Binding Assay: Compounds are also assayed at the β1 and β2 receptors to determine selectivity. All binding assays are run using membranes prepared from CHO cells recombinantly expressing β1 or β2 receptors. Cells are grown for 3-4 days post splitting; the attached cells are washed with PBS and then lysed in 1 mM Tris, pH 7.2 for 10 minutes on ice. The flasks are scraped to remove the cells and the cells then homogenized using a Teflon/glass homogenizer. Membranes are collected by centrifuging at 38,000×g for 15 minutes at 4° C. The pelleted membranes are resuspended in TME buffer (50 mM Tris, pH 7.4, 5 mM $MgCl_2$, 2 mM EDTA) at a concentration of 1 mg protein/mL. Large batches of membranes can be prepared, aliquoted and stored at −70° C. for up to a year without loss of potency. The binding assay is performed by incubating together membranes (2-5 μg of protein), the radiolabelled tracer $^{125}$I-cyanopindolol ($^{125}$I-CYP, 45 pM), 200 ug of WGA-PVT SPA beads (GE Healthcare) and the test compounds at final concentrations ranging from 10-10 M to 10-5 M in a final volume of 200 μL of TME buffer containing 0.1% BSA. The assay plate is incubated for 1 h with shaking at RT and then placed in a Perkin Elmer Trilux scintillation counter. The plates are allowed to rest in the Trilux counter for approximately 10 h in the dark prior to counting. Data are analyzed using a standard 4-parameter non-linear regression analysis using either Graphpad Prism software or an internally developed data analysis package. The $IC_{50}$ is defined as the concentration of the title compound capable of inhibiting 50% of the binding of the radiolabelled tracer ($^{125}$I-CYP). A compound's selectivity for the β3 receptor may be determined by calculating the ratio ($IC_{50}$ β1 AR, β2 AR)/($EC_{50}$ β3 AR).

The following examples are provided to illustrate the invention and are not to be construed as limiting the scope of the invention in any manner.

EXAMPLE 1

(1S)-2-phenoxy-1[(2R,5S)-5-(4-{[1R,5S,6s)-6-(1H-tetrazol-1-yl)-3-azabicyclo[3.1.0]hex-3-yl]carbonyl}benzyl)pyrrolidin-2-yl]ethanol

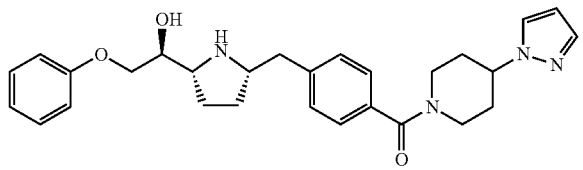 [SMILES: O=C(c1ccc(C[C@@H]2CC[C@H]([C@H](O)COc3ccccc3)N2)cc1)N1CCC(n2cccn2)CC1]

Step A: tert-butyl (2R,5S)-2-((1S)-1-{[tert-butyl(dimethyl)silyl]oxy}-2-phenoxyethyl)-5-(4-{[(1R,5S,6s)-6-(1H-tetrazol-1-yl)-3-azabicyclo[3.1.0]hex-3-yl]carbonyl}benzyl)pyrrolidine-1-carboxylate

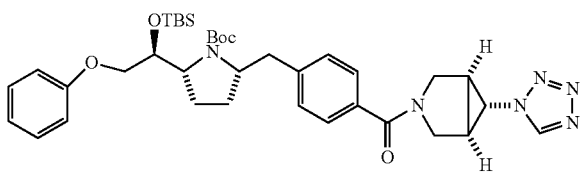

To a solution of 4-{[2S,5R)-1-(tert-butoxycarbonyl)-5-((1S)-1-{[tert-butyl(dimethyl)silyl]oxy}-2-phenoxyethyl)pyrrolidin-2-yl]methyl}benzoic acid, i-3, (18 mg, 0.032 mM) and 4-(1H-pyrazol-1-yl)piperidine, i-4, (20 mg, 0.11 mM) in 1 mL DMF was added HATU (24.6 mg, 0.065 mM) and triethyl amine (0.023 ml, 0.162 mM). The resulting mixture was stirred for 1 h; then the reaction solution was diluted with water and CH3CN. The crude solution was purified by Gilson RP HPLC to give 15 mg of title compound. LC-MS: m/z 589.25 (M-Boc+1).

Step B: (1S)-2-phenoxy-1-[(2R,5S)-5-(4-{[1R,5S,6s)-6-(1H-tetrazol-1-yl)-3-azabicyclo[3.1.0]hex-3-yl]carbonyl}benzyl)pyrrolidin-2-yl]ethanol

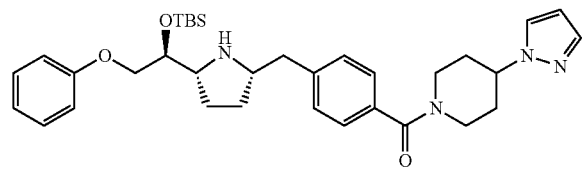 [SMILES: CC(C)(C)[Si](C)(C)O[C@H](COc1ccccc1)[C@H]1CC[C@@H](Cc2ccc(C(=O)N3CCC(n4cccn4)CC3)cc2)N1]

The product from step A (15 mg, 0.022 mM) in 2 ml of methylene chloride was treated with 1 ml of trifluoroacetic acid (TEA), for 3 h. All volatiles were removed in vacuo and the residue was purified by Gilson RH HPLC to yield 9 mg of title compound. LC-MS: m/z 475.19 (M+1).

Using the Beta-3 agonist in vitro functional assay described above the human Beta-3 agonist functional activity of this Example was determined to be between 1 to 10 nM.

EXAMPLES 2-6

Using procedures similar to those described above for Example 1, Examples 2-6 were prepared from the appropriate starting materials.

Using the Beta-3 agonist in vitro functional assay described above the human Beta-3 agonist functional activity of each compound was determined and shown in Table 2 as the following ranges:

less than 1 nM (+);
1-10 nM (++);
11-100 nM (+++), and
greater than 101 nM but less than 1000 nM (++++).

TABLE 2

| Example (Ex.) # | R | MW | MS (MH)+ | Human β3 agonist functional activity |
|---|---|---|---|---|
| 2 | (piperidine-triazole) | 475.2 | 476.2 | ++ |
| 3 | (piperidine-triazole) | 475.2 | 476.2 | +++ |
| 4 | (piperidine-methyltetrazole) | 490.2 | 491.2 | + |
| 5 | (bicyclic tetrazole) | 474.5 | 475.4 | + |
| 6 | (piperazine-methylpyrimidine) | 500.3 | 501.3 | ++ |

While the invention has been described and illustrated with reference to certain particular embodiments thereof, those skilled in the art will appreciate that various changes, modifications and substitutions can be made therein without departing from the spirit and scope of the invention. For example, effective dosages other than the particular dosages as set forth herein above may be applicable as a consequence of variations in the responsiveness of the mammal being treated for any of the indications for the active agents used in the instant invention as indicated above. Likewise, the specific pharmacological responses observed may vary according to and depending upon the particular active compound selected or whether there are present pharmaceutical carriers, as well as the type of formulation employed, and such expected variations or differences in the results are contemplated in accordance with the objects and practices of the present invention. It is intended, therefore, that the invention be defined by the scope of the claims which follow and that such claims be interpreted as broadly as is reasonable.

What is claimed is:
1. A compound of Formula I, or a pharmaceutically acceptable salt thereof, or a stereoisomer thereof, or a pharmaceutically acceptable salt of the stereoisomer thereof:

(I)

[Chemical structure showing: (R¹)ₘ-A-phenyl-O-CH₂-CH(OH)-pyrrolidine(NH)-CH₂-phenyl(R²)q-C(=O)-N-ring(B¹) with R³, R⁶, R⁹ substituents]

wherein m is 0 or 1;
n is 0, 1, or 2;
q is 0 or 1;
A is —CH= or —N=;
$B^1$ is —CH$_2$— or —NH—;
$R^6$ and $R^9$ are each a hydrogen;
or $R^6$ and $R^9$ form a direct bond;
each occurrence of $R^1$ and $R^2$ is independently selected from the group consisting of:
  (1) $C_1$-$C_4$ alkyl optionally substituted with 1 to 3 halogen atoms, and
  (2) halogen;
each occurrence of $R^3$ is independently selected from the group consisting of:
  (1) $C_1$-$C_4$ alkyl optionally substituted with 1 to 3 groups independently selected from:
    (a) halogen,
    (b) —OR$^a$, and
    (c) a 5- to 6-membered heterocyclic ring with 1 to 4 nitrogen atoms, optionally substituted with 1 to 3 groups independently selected from halogen, $C_1$-$C_4$ alkyl optionally substituted with 1 to 3 halogen atoms,
  (2) halogen,
  (3) —OR$^a$,
  (4) —NR$^a$R$^b$, and
  (5) a 5- to 6-membered heterocyclic ring with 1 to 4 nitrogen atoms, optionally substituted with 1 to 3 groups independently selected from
    (a) $C_1$-$C_4$ alkyl optionally substituted with 1 to 3 halogen atoms,
    (b) halogen,
    (c) —OR$^a$, and
    (d) —NR$^a$R$^b$; and
each occurrence of $R^a$ and $R^b$ is independently selected from the group consisting of:
  (1) hydrogen, and
  (2) $C_1$-$C_4$ alkyl optionally substituted with 1 to 3 halogen atoms.

2. The compound of claim 1, wherein:
m is 0;
n is 0, 1, or 2;
q is 0;
A is —CH=;
each occurrence of $R^3$ is independently selected from the group consisting of:
  (1) $C_1$-$C_4$ alkyl optionally substituted with 1 to 3 groups independently selected from:
    (a) halogen,
    (b) —OR$^a$, and
    (c) a 5- to 6-membered heterocyclic ring with 1 to 4 nitrogen atoms, optionally substituted with 1 to 3 groups independently selected from halogen, $C_1$-$C_4$ alkyl optionally substituted with 1 to 3 halogen atoms,
  (2) halogen, and
  (3) a 5- to 6-membered heterocyclic ring with 1 to 4 nitrogen atoms, optionally substituted with 1 to 3 groups independently selected from
    (a) $C_1$-$C_4$ alkyl optionally substituted with 1 to 3 halogen atoms,
    (b) halogen,
    (c) —OR$^a$, and
    (d) —NR$^a$R$^b$; and
each occurrence of $R^a$ and $R^b$ is independently selected from the group consisting of:
  (1) hydrogen,
  (2) methyl, and
  (3) ethyl.

3. The compound of claim 2, wherein:
n is 0 or 1;
each occurrence of $R^3$ is independently selected from the group consisting of:
  (1) $C_1$-$C_4$ alkyl optionally substituted with 1 to 2 groups independently selected from:
    (a) halogen, and
    (b) a 5- to 6-membered heterocyclic ring with 1 to 4 nitrogen atoms selected from the group consisting of pyridyl, dihydropyridyl, 1,2,4-triazolyl, 1,2,3-triazolyl, tetrazolyl, pyrimidinyl, dihydropyrimidinyl, tetrahydropyrimidinyl, pyrazinyl, dihydropyrazinyl, pyridazinyl dihydropyridazinyl, pyrrolidinyl, imidazolyl, pyrazolyl, wherein said 5- to 6-membered heterocyclic ring is optionally substituted with 1 to 3 groups independently selected from halogen and $C_1$-$C_4$ alkyl,
  (2) halogen, and
  (3) a 5- to 6-membered heterocyclic ring with 1 to 4 nitrogen atoms selected from the group consisting of pyridyl, dihydropyridyl, 1,2,4-triazolyl, 1,2,3-triazolyl, tetrazolyl, pyrimidinyl, dihydropyrimidinyl, tetrahydropyrimidinyl, pyrazinyl, dihydropyrazinyl, pyridazinyl dihydropyridazinyl, pyrrolidinyl, imidazolyl, pyrazolyl; wherein said 5- to 6-membered heterocyclic ring is optionally substituted with 1 to 3 groups independently selected from
    (a) $C_1$-$C_4$ alkyl, and
    (b) halogen.

4. The compound of claim 3, wherein
$R^3$ is selected from the group consisting of:
  (1) $C_1$-$C_4$ alkyl optionally substituted with 1 to 2 5- to 6 -membered heterocyclic ring with 1 to 4 nitrogen atoms, and
  (2) a 5- to 6-membered heterocyclic ring with 1 to 4 nitrogen atoms selected from the group consisting of pyridyl, dihydropyridyl, 1,2,4-triazolyl, 1,2,3-triazolyl, tetrazolyl, pyrimidinyl, dihydropyrimidinyl, tetrahydropyrimidinyl, pyrazinyl, dihydropyrazinyl, pyridazinyl dihydropyridazinyl, pyrrolidinyl, imidazolyl, pyrazolyl, wherein said 5- to 6-membered heterocyclic ring is optionally substituted with 1 to 2 $C_1$-$C_4$ alkyl groups.

5. The compound of claim 1 having Formula Ia:

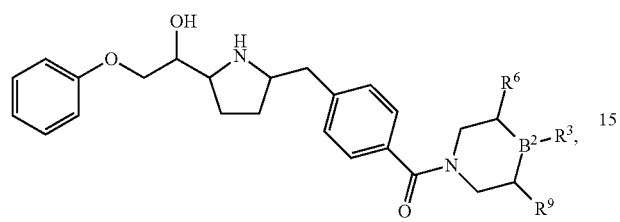

(Ia)

wherein B² is —CH— or —N—;
R⁶ and R⁹ are each a hydrogen;
or R⁶ and R⁹ form a direct bond; and
R³ is selected from the group consisting of:
  (1) methyl optionally substituted with 1 to 2 5- to 6-membered heterocyclic ring with 1 to 4 nitrogen atoms,
  (2) ethyl optionally substituted with 1 to 2 5- to 6-membered heterocyclic ring with 1 to 4 nitrogen atoms; and
  (3) a 5- to 6-membered heterocyclic ring with 1 to 4 nitrogen atoms selected from the group consisting of pyridyl, dihydropyridyl, 1,2,4-triazolyl, 1,2,3-triazolyl, tetrazolyl, pyrimidinyl, dihydropyrimidinyl, tetrahydropyrimidinyl, pyrazinyl, dihydropyrazinyl, pyridazinyl dihydropyridazinyl, pyrrolidinyl, imidazolyl, pyrazolyl, wherein said 5-to6-membered heterocyclic ring is optionally substituted with 1 to 2 groups independently selected from methyl, ethyl, propyl and halogen.

6. The compound of claim 5, wherein:
B² is —CH—; and
R³ is selected from the group consisting of pyridyl, dihydropyridyl, 1,2,4-triazolyl, 1,2,3triazolyl, tetrazolyl, pyrimidinyl, dihydropyrimidinyl, tetrahydropyrimidinyl, pyrazinyl, dihydropyrazinyl, and pyridazinyl, wherein R³ is optionally substituted with 1 to 2 groups independently selected from methyl, ethyl, propyl and halogen.

7. A compound of Formula (Ib), or a pharmaceutically acceptable salt thereof, wherein R is selected from the following table:

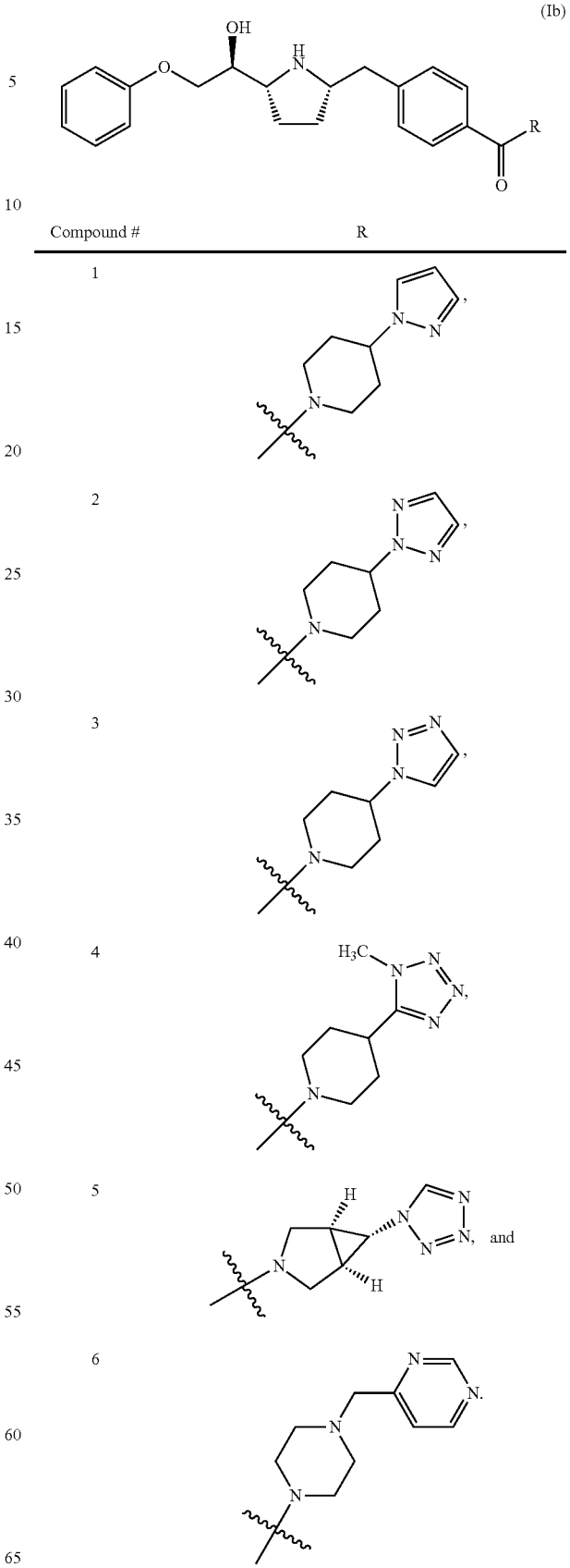

8. A pharmaceutical composition comprising a compound of claim 1 and a pharmaceutically acceptable carrier.

* * * * *